US005777085A

United States Patent [19]
Co et al.

[11] Patent Number: 5,777,085
[45] Date of Patent: Jul. 7, 1998

[54] HUMANIZED ANTIBODIES REACTIVE WITH GPIIB/IIIA

[75] Inventors: Man Sung Co, Cupertino; J. Yun Tso, Menlo Park, both of Calif.

[73] Assignee: Protein Design Labs, Inc., Mountain View, Calif.

[21] Appl. No.: 458,516

[22] Filed: May 17, 1995

Related U.S. Application Data

[63] Continuation of Ser. No. 59,159, May 3, 1993, abandoned, which is a continuation-in-part of Ser. No. 944,159, Sep. 11, 1992, abandoned, which is a continuation-in-part of Ser. No. 895,952, Jun. 9, 1992, abandoned, which is a continuation-in-part of Ser. No. 812,111, Dec. 20, 1991, abandoned.

[51] Int. Cl.$^6$ ............ C07K 16/18; C07K 16/28; C12P 5/10; C07H 21/04
[52] U.S. Cl. ............ 530/388.23; 530/287.3; 530/388.7; 435/69.1; 435/172.3; 435/320.1; 435/326; 435/328; 435/334; 435/343; 536/23.53
[58] Field of Search ............ 424/130.1, 133.1, 424/134.1, 141.1, 143.1, 145.1, 152.1, 172.1; 435/70.21, 171.2, 69.1, 172.3, 320.1, 310.1; 536/23.5, 23.53; 530/387.1, 387.3, 388.1, 388.7, 388.23

[56] References Cited

FOREIGN PATENT DOCUMENTS

| 239400 | 9/1987 | European Pat. Off. ........ C12N 15/00 |
| 0 255 694 | 2/1988 | European Pat. Off. . |
| WO89/11538 | 11/1989 | WIPO ............ C12P 21/00 |
| WO90/07861 | 7/1990 | WIPO ............ C12P 21/00 |

OTHER PUBLICATIONS

Coller et al., "A murine monoclonal antibody that completely blocks the binding of fibrinogen to platelets produces a thrombasthenic–like state in normal platelets and binds to glycoproteins IIb and/or IIIa," *J. Clin. Invest.* 72:325–338 (1983).

Coller et al., "Abolition of in vitro platelet thrombus formation in primates with monoclonal antibodies to the platelet GPIIb/IIIa receptor," *Circulation* 80(6):1766–1774 (1989).

Coller et al., "Antithrombotic effect of a monoclonal antibody to the platelet glycoprotein IIb/IIIa receptor in an experimental animal model," *Blood* 68(3):783–786 (1986).

Co et al., "Humanized antibodies for antiviral therapy," *Proc. Natl. Acad. Sci. USA* 88:2869–2873 (1991).

Daugherty et al., "Polymerase chain reaction facilitates the cloning, CDR–grafting, and rapid expression of a murine monoclonal antibody directed against the CD18 component of leukocyte integrins," *Nuc. Acids Res.* 19:2471–2476 (1991).

Gorman et al., "Reshaping a therapeutic CD4 antibody," *Proc. Natl. Acad. Sci.* 88:4181–4185 (1991).

Harris et al., "Therapeutic antibodies—the coming of age," *Tibtech* 11:42–44 (1993).

Heinrich et al., "Monoclonal antibodies against human platelet membrane glycoproteins IIb–IIIa (II. Different Effects on Platelet Function)," *Thrombosis Research* 38:547–559 (1985).

Jones et al., "Replacing the complementarity–determining regions in a human antibody with those from a mouse," *Nature* 321:522–525 (1986).

Kettleborough et al., "Humanization of a mouse monoclonal antibody by CDR–grafting: the importance of framework residues on loop conformation," *Protein Engineering* 4:773–783 (1991).

Nugent et al., "A human monoclonal autoantibody recognizes a neoantigen on glycoprotein IIIA expressed on stored and activated platelets," *Blood* 70(1):16–22 (1987).

Pidard et al., "Interaction of AP–2, a monoclonal antibody specific for the human platelet glycoprotein IIb–IIIa complex, with intact platelets," *J. of Bio. Chemistry*, 258(20):12582–12586 (1983).

Queen et al., "A humanized antibody that binds to the interleukin 2 receptor," *Proc. Natl. Acad. Sci. USA* 86:10029–10033 (1989).

Riechmann et al., "Reshaping human antibodies for therapy," *Nature* 332:323–327 (1988).

Routledge et al., "A humanized monovalent CD3 antibody which can activate homologous complement," *Eur. J. Immunol.* 21: 2717–2725 (1991).

Shearman et al., "Construction, expression and characterization of humanized antibodies directed against the human α/β T cell receptor," *J. Immunol.* 147(12):4366–4373 (1991).

Tempest et al., "Reshaping a human monoclonal antibody to inhibit human respiratory syncytial virus infection in vivo," *Bio/Technology* 9:226–271 (1991).

S. Bhattacharya et al., "Chimeric humanized monoclonal antiplatelet antibody 7E3 produces prolonged dose–dependent inhibition of platelet function," *Eur. Heart J.*, 12(Abstr. Suppl):26 (1991). (Abstracts selected for presentation at the XIIIth Congress of the European Society of Cardiology, Amsterdam, Netherlands, Aug. 18–22, 1991).

T. Kunicki et al., "Nucleotide sequence of the human autoantibody 2E7 specific for the platelet integrin IIb heavy chain," *J. Autoimmun.*, 4(3):433–446 (Jun., 1991).

R. Taub et al., "A monoclonal antibody against the platelet fibrinogen receptor contains a sequence that mimics a receptor recognition domain in fibrinogen," *J. Biol. Chem.*, 264(1):259–265 (Jan. 5, 1989).

64th Scientific sessions of the American Heart Association, Anaheim, California, USA, Nov. 11–14, 1991. Circulation 84 (4 Suppl.), 1991.

Yano et al. Japan J. Thromb Hemostas. 2:403 (1991).
Co et al. J. Immunol. 152: 2968–2976 (1994).

*Primary Examiner*—Lila Feisee
*Assistant Examiner*—Phillip Gambel
*Attorney, Agent, or Firm*—Townsend & Townsend & Crew

[57] ABSTRACT

Humanized immunoglobulins specifically reactive with GPIIb/IIIa proteins are prepared employing recombinant DNA technology for use in, e.g., treatment of various thrombosis-related disorders.

17 Claims, 14 Drawing Sheets

Fig. 2A

```
                        .         30         .         .        60
ATGATGTCCTCTGCTCAGTTCCTTGGTTTCCTGTTGCTCTGTTTTCAAGGTACCAGATGT
 M  M  S  S  A  Q  F  L  G  F  L  L  L  C  F  Q  G  T  R  C
                        .         90         .         .       120
GATATCCAGATGACACAGACTACATCCTCCCTGTCTGCCTCTCTGGGAGACAGAGTCACC
 D  I  Q  M  T  Q  T  T  S  S  L  S  A  S  L  G  D  R  V  T
                        .        150         .         .       180
ATCAGTTGCAGGGCAAGTCAGGACATTAACAATTATTTAAACTGGTATCAGCAGAAACCA
 I  S  C  R  A  S  Q  D  I  N  N  Y  L  N  W  Y  Q  Q  K  P
                        .        210         .         .       240
GATGGAATTGTTAAACTCCTGATCTACTACACATCAACATTACACTCAGGAGTCCCATCA
 D  G  I  V  K  L  L  I  Y  Y  T  S  T  L  H  S  G  V  P  S
                        .        270         .         .       300
AGGTTCAGTGGCAGTGGGTCTGGAACAGATTATTCTCTCACCATTAGCAACCTGGAGCAG
 R  F  S  G  S  G  S  G  T  D  Y  S  L  T  I  S  N  L  E  Q
                        .        330         .         .       360
GAAGATATTGCCACTTACTTTTGCCAACAGGGTAATACGCTTCCGTGGACGTTCGGTGGA
 E  D  I  A  T  Y  F  C  Q  Q  G  N  T  L  P  W  T  F  G  G

GGCACCAAGCTGGAAATCAAA
 G  T  K  L  E  I  K
```

Fig. 2B

```
                        .         30         .         .        60
ATGGAATGGAGCGGAGTCTTTATCTTTCTTCTGTCAGTGACTGCAAGTGTTCACTCCCAG
 M  E  W  S  G  V  F  I  F  L  L  S  V  T  A  S  V  H  S  Q
                        .         90         .         .       120
GTCCAGCTGCAGCAGTCTGGAGCTGAGCTGGTAGGGCCTGGGACTTCAGTGAGGGTGTCC
 V  Q  L  Q  Q  S  G  A  E  L  V  G  P  G  T  S  V  R  V  S
                        .        150         .         .       180
TGCAAGGCTTCTGGATACGCCTTCACTAATTACTTGATAGAGTGGGTAAAGCAGAGGCCT
 C  K  A  S  G  Y  A  F  T  N  Y  L  I  E  W  V  K  Q  R  P
                        .        210         .         .       240
GGACAGGGCCTTGAGTGGATTGGAGTGATTTATCCTGGAAGTGGTGGTACTAACTACAAT
 G  Q  G  L  E  W  I  G  V  I  Y  P  G  S  G  G  T  N  Y  N
                        .        270         .         .       300
GAGAAGTTCAAGGGCAAGGCAACTCTGACTGTAGACAAATCCTCCACCACTGCCTACATG
 E  K  F  K  G  K  A  T  L  T  V  D  K  S  S  T  T  A  Y  M
                        .        330         .         .       360
CAACTCAGCAGCCTGACATCTGATGACTCTGCGGTCTATTTCTGTGCAAGACGAGATGGT
 Q  L  S  S  L  T  S  D  D  S  A  V  Y  F  C  A  R  R  D  G
                        .        390         .         .
AACTACGGATGGTTTGCCTACTGGGGCCGGGGGACTCTGGTCACTGTCTCTGCA
 N  Y  G  W  F  A  Y  W  G  R  G  T  L  V  T  V  S  A
```

Fig. 5A

```
ASP ILE GLN MET THR GLN THR PRO SER THR LEU SER ALA SER VAL GLY ASP ARG VAL THR
 |   |   |   |   |   |   |       |   |   |   |       |   |   |   |   |   |
ASP ILE GLN MET THR GLN THR THR SER SER LEU SER ALA SER LEU GLY ASP ARG VAL THR
 1                       ⎯⎯⎯              10                                    20

ILE SER CYS ARG ALA SER GLN ASP ILE ASN ASN TYR LEU ASN TRP TYR GLN GLN LYS PRO
 |   |   |   |   |   |   |   |   |   |   |   |   |   |   |   |   |   |   |   |
ILE SER CYS ARG ALA SER GLN ASP ILE ASN ASN TYR LEU ASN TRP TYR GLN GLN LYS PRO
21      ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ 30                       40

GLY LYS ALA PRO LYS LEU LEU ILE TYR TYR THR SER THR LEU HIS SER GLY VAL PRO SER
         |       |   |   |   |   |   |   |   |   |   |   |   |   |   |   |   |
ASP GLY ILE VAL LYS LEU LEU ILE TYR TYR THR SER THR LEU HIS SER GLY VAL PRO SER
41                           ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ 50                60

ARG PHE SER GLY SER GLY SER GLY THR ASP TYR THR LEU THR ILE SER SER LEU GLN PRO
 |   |   |   |   |   |   |   |   |   |   |       |   |   |   |       |   |   |
ARG PHE SER GLY SER GLY SER GLY THR ASP TYR SER LEU THR ILE SER ASN LEU GLU GLN
61          ⎯⎯⎯                          ⎯⎯⎯ ⎯⎯⎯                                 70                                    80

ASP ASP PHE ALA THR TYR PHE CYS GLN GLN GLY ASN THR LEU PRO TRP THR PHE GLY GLN
 |           |   |   |   |   |   |   |   |   |   |   |   |   |   |   |   |
GLU ASP ILE ALA THR TYR PHE CYS GLN GLN GLY ASN THR LEU PRO TRP THR PHE GLY GLY
81                          ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ ⎯⎯⎯ 90                                       100

GLY THR LYS VAL GLU VAL LYS
 |   |   |       |       |
GLY THR LYS LEU GLU ILE LYS
101                     107
```

Fig. 5B

```
GLN VAL GLN LEU VAL GLN SER GLY ALA GLU VAL LYS LYS PRO GLY SER SER VAL LYS VAL
 |   |   |   |   |   |   |   |   |   |           |   |       |   |       |
GLN VAL GLN LEU GLN GLN SER GLY ALA GLU LEU VAL GLY PRO GLY THR SER VAL ARG VAL
1                                   10                                      20

SER CYS LYS ALA SER GLY TYR ALA PHE THR ASN TYR LEU ILE GLU TRP VAL ARG GLN ALA
 |   |   |   |   |   |   |   |   |   |   |   |   |   |   |   |       |       |
SER CYS LYS ALA SER GLY TYR ALA PHE THR ASN TYR LEU ILE GLU TRP VAL LYS GLN ARG
21                              30                                          40

PRO GLY GLN GLY LEU GLU TRP ILE GLY VAL ILE TYR PRO GLY SER GLY GLY THR ASN TYR
 |   |   |   |   |   |   |   |   |   |   |   |   |   |   |   |   |   |   |   |
PRO GLY GLN GLY LEU GLU TRP ILE GLY VAL ILE TYR PRO GLY SER GLY GLY THR ASN TYR
41                              50                                          60

ASN GLU LYS PHE LYS GLY ARG VAL THR LEU THR VAL ASP GLU SER THR ASN THR ALA TYR
 |   |   |   |   |   |           |   |   |   |       |           |   |   |   |
ASN GLU LYS PHE LYS GLY LYS ALA THR LEU THR VAL ASP LYS SER SER THR THR ALA TYR
61                              70                                          80

MET GLU LEU SER SER LEU ARG SER GLU ASP THR ALA VAL TYR PHE CYS ALA ARG ARG ASP
 |       |   |   |   |       |       |       |   |   |   |   |   |   |   |   |
MET GLN LEU SER SER LEU THR SER ASP ASP SER ALA VAL TYR PHE CYS ALA ARG ARG ASP
81                              90                                          100

GLY ASN TYR GLY TRP PHE ALA TYR TRP GLY GLN GLY THR LEU VAL THR VAL SER SER
 |   |   |   |   |   |   |   |   |       |   |   |   |   |   |   |   |
GLY ASN TYR GLY TRP PHE ALA TYR TRP GLY ARG GLY THR LEU VAL THR VAL SER ALA
101                             110                                     119
```

Fig. 5C

```
ASP ILE GLN MET THR GLN THR PRO SER THR LEU SER ALA SER VAL GLY ASP ARG VAL THR
 1                          10                                              20
ILE SER CYS ARG ALA SER GLN ASP ILE ASN ASN TYR LEU ASN TRP TYR GLN GLN LYS PRO
 21                         30                                              40
GLY LYS ALA PRO LYS LEU LEU ILE TYR TYR THR SER THR LEU HIS SER GLY VAL PRO SER
 41                         50                                              60
ARG PHE SER GLY SER GLY SER GLY THR ASP TYR THR LEU THR ILE SER SER LEU GLN PRO
 61                         70                                              80
ASP ASP PHE ALA THR TYR PHE CYS GLN GLN GLY ASN THR LEU PRO TRP THR PHE GLY GLN
 81                         90                                              100
GLY THR LYS VAL GLU VAL LYS ARG THR VAL ALA ALA PRO SER VAL PHE ILE PHE PRO PRO
101                         110                                             120
SER ASP GLU GLN LEU LYS SER GLY THR ALA SER VAL VAL CYS LEU LEU ASN ASN PHE TYR
121                         130                                             140
PRO ARG GLU ALA LYS VAL GLN TRP LYS VAL ASP ASN ALA LEU GLN SER GLY ASN SER GLN
141                         150                                             160
GLU SER VAL THR GLU GLN ASP SER LYS ASP SER THR TYR SER LEU SER SER THR LEU THR
161                         170                                             180
LEU SER LYS ALA ASP TYR GLU LYS HIS LYS VAL TYR ALA CYS GLU VAL THR HIS GLN GLY
181                         190                                             200
LEU SER SER PRO VAL THR LYS SER PHE ASN ARG GLY GLU CYS
201                         210             214
```

Fig. 5D

```
GLN VAL GLN LEU VAL GLN SER GLY ALA GLU VAL LYS LYS PRO GLY SER SER VAL LYS VAL
1                                   10                                      20
SER CYS LYS ALA SER GLY TYR ALA PHE THR ASN TYR LEU ILE GLU TRP VAL ARG GLN ALA
21                                  30                                      40
PRO GLY GLN GLY LEU GLU TRP ILE GLY VAL ILE TYR PRO GLY SER GLY GLY THR ASN TYR
41                                  50                                      60
ASN GLU LYS PHE LYS GLY ARG VAL THR LEU THR VAL ASP GLU SER THR ASN THR ALA TYR
61                                  70                                      80
MET GLU LEU SER SER LEU ARG SER GLU ASP THR ALA VAL TYR PHE CYS ALA ARG ARG ASP
81                                  90                                      100
GLY ASN TYR GLY TRP PHE ALA TYR TRP GLY GLN GLY THR LEU VAL THR VAL SER SER ALA
101                                 110                                     120
SER THR LYS GLY PRO SER VAL PHE PRO LEU ALA PRO SER SER LYS SER THR SER GLY GLY
121                                 130                                     140
THR ALA ALA LEU GLY CYS LEU VAL LYS ASP TYR PHE PRO GLU PRO VAL THR VAL SER TRP
141                                 150                                     160
ASN SER GLY ALA LEU THR SER GLY VAL HIS THR PHE PRO ALA VAL LEU GLN SER SER GLY
161                                 170                                     180
LEU TYR SER LEU SER SER VAL VAL THR VAL PRO SER SER SER LEU GLY THR GLN THR TYR
181                                 190                                     200
ILE CYS ASN VAL ASN HIS LYS PRO SER ASN THR LYS VAL ASP LYS LYS VAL GLU PRO LYS
201                                 210                                     220
SER CYS ASP LYS THR HIS THR CYS PRO PRO CYS PRO ALA PRO GLU LEU LEU GLY GLY PRO
221                                 230                                     240
SER VAL PHE LEU PHE PRO PRO LYS PRO LYS ASP THR LEU MET ILE SER ARG THR PRO GLU
241                                 250                                     260
VAL THR CYS VAL VAL VAL ASP VAL SER HIS GLU ASP PRO GLU VAL LYS PHE ASN TRP TYR
261                                 270                                     280
VAL ASP GLY VAL GLU VAL HIS ASN ALA LYS THR LYS PRO ARG GLU GLU GLN TYR ASN SER
281                                 290                                     300
THR TYR ARG VAL VAL SER VAL LEU THR VAL LEU HIS GLN ASP TRP LEU ASN GLY LYS GLU
301                                 310                                     320
TYR LYS CYS LYS VAL SER ASN LYS ALA LEU PRO ALA PRO ILE GLU LYS THR ILE SER LYS
321                                 330                                     340
ALA LYS GLY GLN PRO ARG GLU PRO GLN VAL TYR THR LEU PRO PRO SER ARG ASP GLU LEU
341                                 350                                     360
THR LYS ASN GLN VAL SER LEU THR CYS LEU VAL LYS GLY PHE TYR PRO SER ASP ILE ALA
361                                 370                                     380
VAL GLU TRP GLU SER ASN GLY GLN PRO GLU ASN ASN TYR LYS THR THR PRO PRO VAL LEU
381                                 390                                     400
ASP SER ASP GLY SER PHE PHE LEU TYR SER LYS LEU THR VAL ASP LYS SER ARG TRP GLN
401                                 410                                     420
GLN GLY ASN VAL PHE SER CYS SER VAL MET HIS GLU ALA LEU HIS ASN HIS TYR THR GLN
421                                 430                                     440
LYS SER LEU SER LEU SER PRO GLY LYS
441                                 449
```

Fig. 6 rh29
TATATCTAGA CCACCATGGG ATGGAGCTGG ATCTTTCTCT TCCTCCTGTC AGGTACCGCG
GGCGTGCACT CTCAGGTCCA GCTTGTCCAG TCTGGCGCTG AAGTCAAGAA ACC rh30
TATAGAATTC TCGAGACCCT GTCCAGGGGC CTGCCTTACC CACTCTATCA AGTAATTAGT
AAAGGCGTAG CCAGAAGCTT TGCAGGAGAC CTTCACGGAG CTCCCAGGTT TCTTGACTTC
AGC rh31
TATAGAATTC TCGAGTGGAT TGGAGTGATT TATCCTGGAA GTGGTGGTAC TAACTACAAT
GAGAAGTTCA AGGGCCGTGT TACACTGACA GTAGACGAAT CCACCAATAC AGCCTACATG
GAACTGAGCA GCCTGAGATC A rh32
TATATCTAGA GGTTTTAAGG ACTCACCTGA GGAGACTGTG ACCAGGGTTC CTTGGCCCCA
GTAGGCAAAC CATCCGTAGT TACCATCTCG TCTTGCACAG AAATAGACTG CAGTGTCCTC
TGATCTCAGG CTGCTCA rh33
TATATCTAGA CCACCATGGA GACCGATACC CTCCTGCTAT GGGTCCTCCT GCTATGGGTC
CCAGGATCAA CCGGAGATAT TCAGATGACC CAGACTCCGT CGACCCTCTC TGCTAGC rh34
TATAAAGCTT GGGAGCTTTG CCTGGCTTCT GCTGATACCA GTTTAAATAA TTGTTAATGT
CCTGACTTGC CCTGCAACTT ATGGTGACCC TATCCCCGAC GCTAGCAGAG AGGGTCG rh35
TATAAAGCTT CTAATTTATT ACACATCAAC ATTACACTCA GGGGTACCTT CACGCTTCAG
TGGCAGTGGA TCTGGGACCG ATTATACCCT CACAATCTCG AGTCTGCAGC CAGATGA rh36
TATATCTAGA GCAAAAGTCT ACTTACGTTT GACCTCCACC TTGGTCCCCT GACCGAACGT
CCACGGAAGC GTATTACCCT GTTGGCAAAA ATAAGTGGCG AAATCATCTG GCTGCAGACT

Fig. 7C

```
GLN VAL GLN LEU VAL GLN SER GLY ALA GLU VAL LYS LYS PRO GLY SER SER VAL LYS VAL
 1                          10                                              20
SER CYS LYS ALA SER GLY TYR ALA PHE THR ASN TYR LEU ILE GLU TRP VAL ARG GLN ALA
21                          30                                              40
PRO GLY GLN GLY LEU GLU TRP ILE GLY VAL ILE TYR PRO GLY SER GLY GLY THR ASN TYR
41                          50                                              60
ASN GLU LYS PHE LYS GLY ARG VAL THR LEU THR VAL ASP GLU SER THR ASN THR ALA TYR
61                          70                                              80
MET GLU LEU SER SER LEU ARG SER GLU ASP THR ALA VAL TYR PHE CYS ALA ARG ARG ASP
81                          90                                              100
GLY ASN TYR GLY TRP PHE ALA TYR TRP GLY GLN GLY THR LEU VAL THR VAL SER SER ALA
101                         110                                             120
SER THR LYS GLY PRO SER VAL PHE PRO LEU ALA PRO SER SER LYS SER THR SER GLY GLY
121                         130                                             140
THR ALA ALA LEU GLY CYS LEU VAL LYS ASP TYR PHE PRO GLU PRO VAL THR VAL SER TRP
141                         150                                             160
ASN SER GLY ALA LEU THR SER GLY VAL HIS THR PHE PRO ALA VAL LEU GLN SER SER GLY
161                         170                                             180
LEU TYR SER LEU SER SER VAL VAL THR VAL PRO SER SER SER LEU GLY THR GLN THR TYR
181                         190                                             200
ILE CYS ASN VAL ASN HIS LYS PRO SER ASN THR LYS VAL ASP LYS LYS VAL GLU PRO LYS
201                         210                                             220
SER CYS
221 222
```

Fig. 7D

```
GLN VAL GLN LEU VAL GLN SER GLY ALA GLU VAL LYS LYS PRO GLY SER SER VAL LYS VAL
1                                   10                                      20
SER CYS LYS ALA SER GLY TYR ALA PHE THR ASN TYR LEU ILE GLU TRP VAL ARG GLN ALA
21                                  30                                      40
PRO GLY GLN GLY LEU GLU TRP ILE GLY VAL ILE TYR PRO GLY SER GLY GLY THR ASN TYR
41                                  50                                      60
ASN GLU LYS PHE LYS GLY ARG VAL THR LEU THR VAL ASP GLU SER THR ASN THR ALA TYR
61                                  70                                      80
MET GLU LEU SER SER LEU ARG SER GLU ASP THR ALA VAL TYR PHE CYS ALA ARG ARG ASP
81                                  90                                      100
GLY ASN TYR GLY TRP PHE ALA TYR TRP GLY GLN GLY THR LEU VAL THR VAL SER SER ALA
101                                 110                                     120
SER THR LYS GLY PRO SER VAL PHE PRO LEU ALA PRO SER SER LYS SER THR SER GLY GLY
121                                 130                                     140
THR ALA ALA LEU GLY CYS LEU VAL LYS ASP TYR PHE PRO GLU PRO VAL THR VAL SER TRP
141                                 150                                     160
ASN SER GLY ALA LEU THR SER GLY VAL HIS THR PHE PRO ALA VAL LEU GLN SER SER GLY
161                                 170                                     180
LEU TYR SER LEU SER SER VAL VAL THR VAL PRO SER SER SER LEU GLY THR GLN THR TYR
181                                 190                                     200
ILE CYS ASN VAL ASN HIS LYS PRO SER ASN THR LYS VAL ASP LYS LYS VAL GLU PRO LYS
201                                 210                                     220
SER CYS ASP LYS THR HIS THR CYS PRO PRO CYS PRO ALA PRO GLU
221                                 230                     235
```

HUMANIZED ANTIBODIES REACTIVE WITH GPIIB/IIIA

CROSS REFERENCE TO RELATED APPLICATIONS

This is a Continuation of application Ser. No. 08/059,159, filed May 3, 1993, now abandoned, which is a continuation-in-part of U.S. Ser. No. 07/944,159 filed Sep. 11, 1992, now abandoned, which is a continuation-in-part of U.S. Ser. No. 07/895,952 filed Jun. 9, 1992, now abandoned, which is a continuation-in-part of U.S. Ser. No. 07/812,111 filed Dec. 20, 1991 (now abandoned).

FIELD OF THE INVENTION

The present invention relates generally to the combination of recombinant DNA and monoclonal antibody technologies for developing novel biologics and, more particularly, for example, to the production of non-immunogenic (in humans) immunoglobulins specific for the GPIIb/IIIa antigen and their uses in vitro and in vivo.

BACKGROUND OF THE INVENTION

Cardiovascular disease is a leading cause of death and disability in developed countries. Atherosclerosis, or narrowing and hardening of the arteries, is a major contributor to cardiovascular disease. Arterial thrombosis, the formation of a blood clot or thrombus, commonly occurs in arteries effected by atherosclerosis, especially when a rupture occurs in a plaque that has built up on the vessel wall. The formation of a thrombus in a coronary artery can cause an acute myocardial infarction (heart attack) if the blockage is sustained, or unstable angina if the blockage is transient. A thrombus in a cerebral artery can cause a stroke or a transient ischemic attack. An arterial thrombus is composed of an aggregation of small blood cells called platelets together with the protein fibrin.

The glycoprotein GPIIb/IIIa is found on the surface of platelets and plays a key role in their aggregation and hence the formation of thrombi (see, generally, Phillips et al., Blood 71, 831 (1988), which is incorporated herein by reference). The GPIIb/IIIa complex is composed of one molecule of GPIIb (M.W.=140 kDa), which itself consists of a large (M.W.=125 kDa) and small (M.W.=25 kDa) chain linked by one or more disulfide bonds and one molecule of GPIIIa (M.W.=105 kDa), which is a single polypeptide chain. $Ca^{2+}$ ions are required to maintain the heterodimeric structure of GPIIb/IIIa, which is a member of the integrin family of adhesion molecules. When platelets are activated by a physiological agonist such as thrombin, adenosine diphosphate (ADP) or epinephrine, the structure or environment of the GPIIb/IIIa molecules on the surface of the platelets is altered so they can bind the serum protein fibrinogen. The fibrinogen cross-links the platelets so they form aggregates. GPIIb/IIIa is also a receptor for the adhesive proteins fibronectin, von Willebrand factor and vitronectin, and therefore contributes to the adhesion and spreading of platelets on the subendothelium of injured blood vessels.

A number of mouse monoclonal antibodies have been developed that bind to GPIIb/IIIa and block its ability to bind fibrinogen. These antibodies include 10E5 (Coller et al., J. Clin. Invest. 72, 325 (1983)), AP-2 (Pidard et al., J. Biol. Chem. 258, 12582 (1983)) and 7E3 (Coller, J. Clin. Invest. 76, 101 (1985), which are incorporated herein by reference) and C4G1, described herein. By blocking fibrinogen binding, these antibodies inhibit or abrogate the aggregation of platelets in vitro in response to agonists such as ADP. Anti-GPIIb/IIIa antibodies may therefore inhibit the formation of thrombi by preventing the aggregation of additional platelets. In fact, treatment with the 7E3 antibody has been found to contribute to recanalization of the coronary artery in a canine model of coronary arterial thrombosis, especially when administered in combination with tissue plasminogen activator (tPA) (Gold et al., Circulation 77, 670 (1988)).

Unfortunately, the use of non-human monoclonal antibodies such as 7E3 or C4G1 have certain drawbacks in human treatment, particularly in repeated therapeutic regimens as explained below. Mouse monoclonal antibodies, for example, tend to have a short half-life in humans, and lack other important immunoglobulin functional characteristics when used in humans.

Perhaps more importantly, non-human monoclonal antibodies contain substantial stretches of amino acid sequences that will be immunogenic when injected into a human patient. Numerous studies have shown that, after injection of a foreign antibody, the immune response elicited by a patient against an antibody can be quite strong, essentially eliminating the antibody's therapeutic utility after an initial treatment. Moreover, as increasing numbers of different mouse or other antigenic (to humans) monoclonal antibodies can be expected to be developed to treat various diseases, after the first or several treatments with any different non-human antibodies, subsequent treatments even for unrelated therapies can be ineffective or even dangerous in themselves, because of cross-reactivity.

While the production of so-called "chimeric antibodies" (e.g., mouse variable regions joined to human constant regions) has proven somewhat successful, a significant immunogenicity problem remains. In general, the production of human immunoglobulins reactive with GPIIb/IIIa antigen with high affinity, as with many antigens, would be extremely difficult using typical human monoclonal antibody production techniques. To date, no information is available concerning human immunoglobulins which are capable of inhibiting the aggregation of platelets and are useful in the treatment of thrombosis as therapeutic agents. Similarly, utilizing recombinant DNA technology to produce so-called "humanized" or "reshaped" antibodies (see, e.g., Riechmann et al., Nature 332, 323 (1988) and EPO Publication No. 0239400, which are incorporated herein by reference), provides uncertain results, in part due to unpredictable binding affinities.

Thus, there is a need for improved forms of humanized immunoglobulins specific for GPIIb/IIIa antigen that are substantially non-immunogenic in humans, yet easily and economically produced in a manner suitable for therapeutic formulation and other uses. The present invention fulfills these and other needs.

SUMMARY OF THE INVENTION

The present invention provides novel compositions useful, for example, in the treatment of arterial thrombosis-related human disorders, the compositions containing humanized immunoglobulins specifically capable of binding to GPIIb/IIIa antigen. The immunoglobulins can have two pairs of light chain/heavy chain complexes, at least one chain comprising one or more mouse complementarity determining regions functionally joined to human framework region segments. For example, mouse complementarity determining regions, with or without additional naturally-associated mouse amino acid residues, can be introduced into human framework regions to produce humanized immunoglobulins capable of binding to the GPIIb/IIIa antigen at affinity levels stronger than about $10^7$ $M^{-1}$. These humanized immunoglobulins will also be capable of blocking the binding of the CDR-donating mouse monoclonal antibody to GPIIb/IIIa.

The immunoglobulins, including binding fragments and other derivatives thereof, of the present invention may be produced readily by a variety of recombinant DNA techniques, with ultimate expression in transfected cells, preferably immortalized eukaryotic cells, such as myeloma or hybridoma cells. Polynucleotides comprising a first sequence coding for humanized immunoglobulin framework regions and a second sequence set coding for the desired immunoglobulin complementarity determining regions can be produced synthetically or by combining appropriate cDNA and genomic DNA segments.

The humanized immunoglobulins may be utilized alone in substantially pure form, or together with a therapeutic agent such as tissue plasminogen activator or aspirin active against thrombi. All of these compounds will be particularly useful in treating acute myocardial infarction, unstable angina, stroke and other platelet-mediated disorders. The humanized immunoglobulins or their complexes can be prepared in a pharmaceutically accepted dosage form, which will vary depending on the mode of administration.

The humanized immunoglobulins may also be utilized together with a labeling moiety for use in diagnosing the presence and location of a thrombus, or certain types of cancer cells which develop GPIIb/IIIa on their surfaces, in a human patient. Such labeling moieties include, but are not limited to, radiopaque dyes, radiocontrast agents, fluorescent molecules, spin-labeled molecules, enzymes, or other labeling moieties of diagnostic value, particularly in radiologic or magnetic resonance imaging techniques.

BRIEF DESCRIPTION OF THE FIGURES

FIGS. 2A and 2B. Sequences of the cDNA and translated amino acid sequences of the light chain (A) [SEQ. ID NOS:4 and 5] and heavy chain (B) [SEQ. ID NOS:6 and 7] variable regions of the antibody C4G1. The CDR sequences are underlined. The mature light chain protein begins with amino acid 21 D and the mature heavy chain protein with amino acid 20 Q, preceded by the respective signal sequences.

FIGS. 5 A–B. Amino acids sequences of the humanized C4G1 light (A) and heavy (B) chain variable domains compared with the mouse C4G1 sequences.

FIGS. 5 C–D. Expected amino acid sequences of the complete light and heavy chains of the humanized C4G1 antibody.

FIG. 6. Oligonucleotides for synthesis of DNA fragments encoding variable regions of humanized C4G1 antibody.

FIGS. 7A–D. Schematic diagrams of the plasmids pHFab.D (A) and pHF(ab')2.D (B), used respectively for expression of heavy chains of the humanized Fab and F(ab')$_2$ fragments. The plasmids are similar to the plasmid pVg1-dhfr (FIG. 3) but pHFab.D contains only $C_H1$ and the first 5 amino acids of the hinge exon of the human $C_{\gamma1}$ gene, followed by a stop codon and splice donor signal; and pHF(ab')2.D contains only $C_H1$, the hinge and the first 2 amino acids of $C_H2$, followed by a stop codon and splice donor signal. The final exon is followed by a region from beyond the mouse γ2a constant region gene that contains a poly A signal. Amino acid sequences of the heavy chain of the Fab fragment (C) [SEQ. ID NO:20] and recombinant F(ab')$_2$ fragment (D) [SEQ. ID NO:21], designated F(ab')$_2$-1, of the humanized C4G1 antibody.

DETAILED DESCRIPTION OF THE INVENTION

Figure 1:
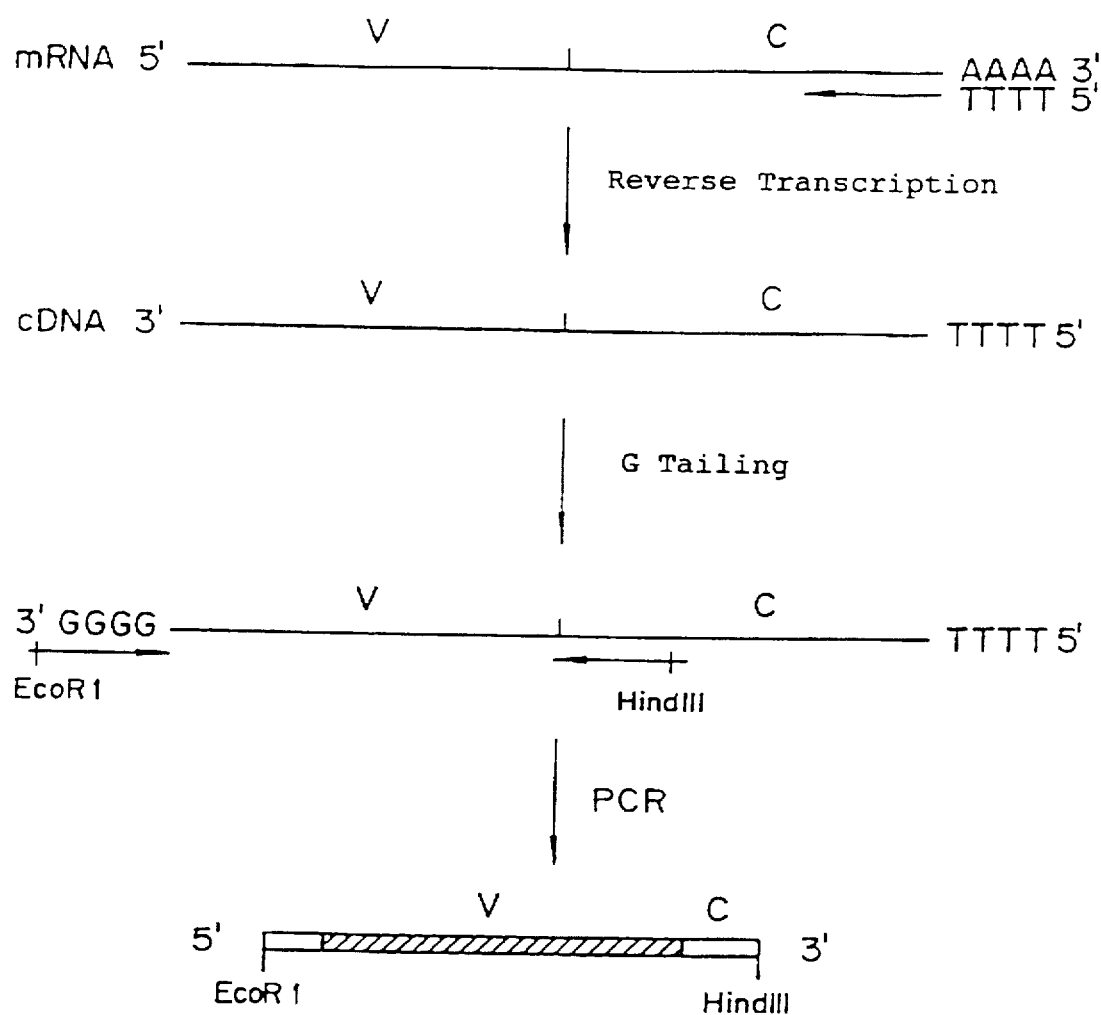
FIG. 1. Scheme for anchored polymerase chain reaction (PCR) cloning of the heavy and light chain variable domain cDNAs. RNA was prepared from about $10^7$ hybridoma cells using the hot phenol extraction method. Briefly, cells were resuspended and vortexed in 1 ml of RNA extraction buffer (50 mM sodium acetate pH 5.2/1% SDS), extracted with 0.5 ml of phenol pH 5.2 at 65° C. for 15 min, followed by another 15 min. on ice. The aqueous phase was recovered and precipitated twice with ethanol. cDNA was synthesized from 10 ug of total RNA using reverse transcriptase (BRL, Bethesda, MD) and oligo $dT_{12-18}$ (Pharmacia, Piscatway, N.J.) as primers. A poly(dG) tail was attached to the 3' end of the cDNA using terminal deoxynucleotide transferase (BRL) (E. Y. Loh et al., Science 243, 217 (1989)). The variable domain genes (V) were amplified using AmpliTaq (Perkin Elmer-Cetus) with the primer mcO45 (TAATCTAGAATTCCCCCCCCCCCCCCCCC) [SEQ. ID NO:1] that hybridized to the poly(dG) tails and primers that hybridized to the constant region genes (C). For the light chain, the primer used was mcO46 (TATAGAGCTCAAGCTTGGATGGTGGGAAGATGGA-TACAGTTGGTGC) [SEQ. ID NO:2]. For the heavy chain, the primer used was mcO47 (TATAGAGCTCAAGCTTCCAGTGGATAGAC(CAT)GATGGGG(GC)TGT(TC)GTTTTGGC) [SEQ. ID NO:3]. The sequence in parenthesis indicates a base degeneracy. The degeneracy was introduced so that the primer would be able to hybridize to most gamma chains. The amplified fragments were then digested with EcoRI and HindIII and cloned into pUC18 vector for sequencing.

In accordance with the present invention, humanized immunoglobulins specifically reactive with GPIIb/IIIa related epitopes are provided. These immunoglobulins, which have binding affinities to GPIIb/IIIa of at least about $10^7 M^{-1}$, and preferably $10^8 M^{-1}$ to $10^{10} M^{-1}$ or stronger, are capable of, e.g., preventing platelet aggregation. The humanized immunoglobulins will have a human framework and will have one or more complementarity determining regions (CDR's) from an immunoglobulin, typically a mouse immunoglobulin, specifically reactive with GPIIb/IIIa antigen. In a preferred embodiment, one or more of the CDR's will come from the C4G1 antibody. Thus, the immunoglobulins of the present invention, which can be produced economically in large quantities, find use, for example, in the treatment of platelet-mediated disorders in human patients by a variety of techniques.

The basic antibody structural unit is known to comprise a tetramer. Each tetramer is composed of two identical pairs of polypeptide chains, each pair having one "light" (about 25 kD) and one "heavy" chain (about 50-70 kD). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See, generally, *Fundamental Immunology*, Paul, W., Ed., Chapter 7, pgs. 131–166, Raven Press, New York (1984), which is incorporated herein by reference.)

The variable regions of each light/heavy chain pair form the antibody binding site. The chains all exhibit the same general structure of relatively conserved framework regions joined by three hypervariable regions, also called Complementarity Determining Regions or CDR's (see, "Sequences of Proteins of Immunological Interest," Kabat, E., et al., U.S. Department of Health and Human Services. (1987); and Chothia and Lesk, J. Mol. Biol., 196, 901–917 (1987), which are incorporated herein by reference). The CDR's from the two chains of each pair are aligned by the framework regions, enabling binding to a specific epitope.

As used herein, the term "immunoglobulin" refers to a protein consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. The immunoglobulins may exist in a variety of forms besides antibodies; including, for example, Fv, Fab, and F(ab')₂ as well as bifunctional hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879–5883 (1988) and Bird et al., Science, 242, 423–426 (1988), which are incorporated herein by reference). (See, generally, Hood et al., *Immunology*, Benjamin, N.Y., 2nd ed. (1984), Harlow and Lane, *Antibodies. A Laboratory Manual*, Cold Spring Harbor Laboratory (1988) and Hunkapiller and Hood, Nature, 323, 15–16 (1986), which are incorporated herein by reference).

Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as $\gamma_1$ and $\gamma_3$. A typical therapeutic chimeric antibody is thus a hybrid protein consisting of the V or antigen-binding domain from a mouse antibody and the C or effector domain from a human antibody, although other mammalian species may be used.

As used herein, the term "framework region" refers to those portions of immunoglobulin light and heavy chain variable regions that are relatively conserved (i.e., other than the CDR's) among different immunoglobulins in a single species, as defined by Kabat, et al., op. cit. As used herein, a "human framework region" is a framework region that is substantially identical (about 85% or more) to the framework region of a naturally occurring human antibody.

As used herein, the term "humanized immunoglobulin" refers to an immunoglobulin comprising a human framework, at least one CDR from a non-human antibody, and in which any constant region present is substantially identical to a human immunoglobulin constant region, i.e., at least about 85–90%, preferably at least 95% identical. Hence, all parts of a humanized immunoglobulin, except possibly the CDR's, are substantially identical to corresponding parts of one or more native human immunoglobulin sequences. For example, a humanized immunoglobulin would not encompass a chimeric mouse variable region/ human constant region antibody.

Humanized antibodies have at least three potential advantages over mouse and in some cases chimeric antibodies for use in human therapy:

1) because the effector portion is human, it may interact better with the other parts of the human immune system (e.g., destroy the target cells more efficiently by complement-dependent cytotoxicity (CDC) or antibody-dependent cellular cytotoxicity (ADCC)).

2) The human immune system should not recognize the framework or C region of the humanized antibody as foreign, and therefore the antibody response against such an injected antibody should be less than against a totally foreign mouse antibody or a partially foreign chimeric antibody.

3) Injected mouse antibodies have been reported to have a half-life in the human circulation much shorter than the half-life of normal antibodies (Shaw, D. et al., *J. Immunol.* 138, 4534–4538 (1987)). Injected humanized antibodies will presumably have a half-life essentially identical to naturally occurring human antibodies, allowing smaller and less frequent doses to be given.

In one aspect, the present invention is directed to recombinant polynucleotides encoding the heavy and/or light chain CDR's from an immunoglobulin capable of binding to a desired epitope of GPIIb/IIIa antigen, such as monoclonal antibodies C4G1, 7E3, 10E5 or AP-2. The polynucleotides encoding these regions will typically be joined to polynucleotides encoding appropriate human framework regions. As to the human framework region, a framework or variable region amino acid sequence of a CDR-providing non-human immunoglobulin is compared with corresponding sequences in a human immunoglobulin sequence collection, and a sequence having high homology is selected. Exemplary polynucleotides, which on expression code for the polypeptide chains comprising the heavy and light chain CDR's of monoclonal antibody C4G1 are included in FIG. 2. Due to codon degeneracy and non-critical amino-acid substitutions, other polynucleotide sequences can be readily substituted for those sequences, as detailed below. The design of humanized immunoglobulins may be carried out as follows. When an amino acid falls under the following category, the framework amino acid of a human immunoglobulin to be used (acceptor immunoglobulin) is replaced by a framework amino acid from a CDR-providing non-human immunoglobulin (donor immunoglobulin):

(a) the amino acid in the human framework region of the acceptor immunoglobulin is unusual for human immunoglobulin at that position, whereas the corresponding amino acid in the donor immunoglobulin is typical for human immunoglobulin at that position;

(b) the position of the amino acid is immediately adjacent to one of the CDR's; or (c) the amino acid is within about 3 Å of a CDR in a tertiary structure immunoglobulin model (see, Queen et al., op. cit., and Co et al., Proc. Natl. Acad. Sci. USA 88, 2869 (1991), respectively, both of which are incorporated herein by reference). When each of the amino acid in the human framework region of the acceptor immunoglobulin and a corresponding amino acid in the donor immunoglobulin is unusual for human immunoglobulin at that position, such an amino acid is replaced by an amino acid typical for human immunoglobulin at that position. For a detailed description of the production of humanized immunoglobulins (see, Queen et al., op. cit., and Co et al., op. cit.)

The polynucleotides will typically further include an expression control polynucleotide sequence operably linked to the humanized immunoglobulin coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the light chains, heavy chains, light/heavy chain dimers or intact antibodies, binding fragments or other immunoglobulin forms may follow.

The nucleic acid sequences of the present invention capable of ultimately expressing the desired humanized antibodies can be formed from a variety of different polynucleotides (genomic or cDNA, RNA, synthetic oligonucleotides, etc.) and components (e.g., V, J, D, and C regions), as well as by a variety of different techniques. Joining appropriate genomic and synthetic sequences is presently the most common method of production, but CDNA sequences may also be utilized (see, European Patent Publication No. 0239400 and Reichmann, L. et al., Nature 332, 323–327 (1988), both of which are incorporated herein by reference).

Human constant region DNA sequences can be isolated in accordance with well known procedures from a variety of human cells, but preferably immortalized B-cells (see, Kabat op. cit. and WP87/02671). The CDR's for producing the immunoglobulins of the present invention will be similarly derived from monoclonal antibodies capable of binding to GPIIb/IIIa and produced in any convenient mammalian source, including, mice, rats, rabbits, or other vertebrate capable of producing antibodies by well known methods. Suitable source cells for the polynucleotide sequences and host cells for immunoglobulin expression and secretion can be obtained from a number of sources, such as the American Type Culture Collection (*Catalogue of Cell Lines and Hybridomas*, Fifth edition (1985) Rockville, Md., U.S.A., which is incorporated herein by reference).

In addition to the humanized immunoglobulins specifically described herein, other "substantially homologous" modified immunoglobulins can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis (see, Gillman and Smith, Gene 8, 81–97 (1979) and Roberts S. et al, Nature 328, 731–734 (1987), both of which are incorporated herein by reference).

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in the vectors pVk and pVg1-dhfr (FIG. 3) using site-directed mutagenesis, such as after CH1 to produce Fab fragments or after the hinge region to produce F(ab')$_2$ fragments. Single chain antibodies may be produced by joining VL and VH with a DNA linker (see Huston et al., op cit., and Bird et al., op cit.). Also because like many genes, the immunoglobulin-related genes contain separate functional regions, each having one or more distinct biological activities, the genes may be fused to functional regions from other genes to produce fusion proteins having novel properties.

As stated previously, the polynucleotides will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

*E. coli* is one prokaryotic host useful particularly for cloning the polynucleotides of the present invention. Other microbial hosts suitable for use include bacilli, such as *Bacillus subtilus*, and other enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, *From Genes to Clones*, VCH Publishers, New York, N.Y. (1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, preferably myeloma cell lines, etc, or transformed B-cells or hybridomas. Expression vectors for these cells can include expression control sequences, such as an origin of replication, a promoter, an enhancer (Queen et al., Immunol. Rev. 89, 49–68 (1986), which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, cytomegalovirus and the like.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See, generally, Maniatis et al., *Molecular Cloning: A Laboratory Manual*, Cold Spring Harbor Press (1982), which is incorporated herein by reference.)

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see, generally, Scopes, R., *Protein Purification*, Springer-Verlag, New York (1982), which is incorporated herein by reference). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent stainings, and the like. (See, generally, *Immunological Methods*, Vols. I and II, Lefkovits and Pernis, eds., Academic Press, New York, N.Y. (1979 and 1981)).

The immunoglobulins of the present invention will typically find use individually in treating cardiovascular diseases and other thromboembolitic diseases. For example, typical disease states suitable for treatment include acute myocardial infarction, unstable angina, stroke, transient ischemic episodes, deep vein thrombosis and pulmonary embolism (see, generally, Hoffbrand & Pettit, Essential Haematology, Blackwell Scientific Publications, Oxford (1980)). The immunoglobulin may also be used to prevent reocclusion after angioplasty procedures or blood vessel operations and occlusion after or during extracorporeal blood circulation procedures such as dialysis, extracorporeal cardiopulmonary circulation and the like. The immunoglobulins of the present invention will also find use in the treatment of other platelet-mediated disorders, such as nephritis, peripheral circulatory failure, thromboangiitis obliterans, thrombosis after transplantation, chronic arterial obstruction, arteriosclerosis obliterans, coronary sclerosis, congestive heart failure, cerebrovascular spasm and the like. The immunoglobulins may also be used to treat thrombotic thrombocytopenic purpura, HUS and platelet-mediated autoimmune disease, to block metastasis, and to stimulate differentiation or growth of megakaryocytes or megakaryoblasts.

A CDR from a GPIIb/IIIa-binding antibody, which is capable of inhibiting the aggregation of platelets, is preferably used for the humanized immunoglobulin of the present invention. In addition, it is known that antibodies which react with vascular endothelial cells, such as 7E3 and the like antibodies, may cause endothelial cell injury (Annals New York Academy of Science, 614, 204, (1991)). In consequence, it is more preferable to use a CDR originating from C4G1 or the like immunoglobulin so that the antigenic determinant bound by the antibody is present on platelets but is absent or present in reduced amounts on vascular endothelial cells. It is expected that a humanized immunoglobulin of the present invention, such as the humanized immunoglobulin that binds to the antigenic determinant identified by the mouse antibody C4G1, will not cause endothelial cell injury if administered.

In the case of the aggregation of platelets caused by the ADP or adrenaline stimulus, a reversible primary aggregation occurs after the addition of the agonist, followed by a secondary aggregation which is dose-dependently irreversible and is accompanied by a releasing reaction. It is known that 7E3 or the like antibody inhibits the aggregation of platelets when platelets are treated in advance with the antibody. However, an antibody which inhibits the aggregation of platelets when added during the platelet aggregation process has not hitherto been described. It has been found that the C4G1 antibody inhibits not only the primary aggregation, but also the secondary aggregation, when the antibody is added after generation of the primary aggregation. In consequence, it is highly probable that a humanized immunoglobulin containing a CDR from the C4G1 antibody, or an immunoglobulin having similar function to the C4G1 antibody, will also inhibit initial steps of the activation and aggregation of platelets during the acute stage of thrombotic diseases.

It is known that levels of thromboxane $A_2$, PAI-1 and the like in blood increase rapidly after reconstruction of blood flow by means of PTCA, PTCR or the like for the treatment of thrombotic diseases. Activation of platelets and release of various mediators such as TGF-$\beta_1$, PDGF and the like are regarded as important factors in this response. It was found when examined in vitro that the mouse C4G1 antibody is able to inhibit not only the aggregation of platelets caused by ADP stimulus but also the releasing reaction of platelets. In consequence, it is probable that a humanized immunoglobulin prepared by making use of a CDR originated from an immunoglobulin which can inhibit both aggregation of platelets and releasing reaction of platelets, such as the mouse C4G1 antibody, will inhibit not only the aggregation of platelets but also the releasing reaction of platelets when used in humans, thus leading to a possibility of inhibiting side effects after a treatment by reconstruction of blood flow by means such as PTCA, PTCR or the like.

Any humanized immunoglobulins of the present invention may also be used in combination with other antibodies, particularly humanized antibodies reactive with different platelet antigens or clotting factors. For example, suitable antigens to which a cocktail of humanized immunoglobulins may react include VLA-2, VLA-5, GPIb, GPIV, von Willebrand factor, thrombin and the platelet thrombin receptor (see, Coller, New Eng. J. Med. 322, 33 (1990)).

The immunoglobulins can also be used as separately administered compositions given in conjunction with other therapeutic agents. Typically, the agents may include aspirin and heparin, but numerous additional agents (e.g., tPA) well-known to those skilled in the art for treatment of cardiovascular disease may also be utilized.

The humanized immunoglobulins and pharmaceutical compositions thereof of this invention are particularly useful for parenteral administration, i.e., subcutaneously, intramuscularly or intravenously. The compositions for parenteral administration will commonly comprise a solution of the immunoglobulin or a cocktail thereof dissolved in an acceptable carrier, preferably an aqueous carrier. A variety of aqueous carriers can be used, e.g., water, buffered water, 0.4% saline, 0.3% glycine, 5% glucose, human albumin solution and the like. These solutions are sterile and generally free of particulate matter. These compositions may be sterilized by conventional, well-known sterilization techniques. The compositions may contain pharmaceutically acceptable auxiliary substances as required to approximate physiological conditions such as pH adjusting and buffering agents, tonicity agents, toxicity adjusting agents and the like, for example sodium acetate, sodium chloride, potassium chloride, calcium chloride, sodium lactate, sodium citrate, etc. The concentration of immunoglobulin in these formulations can vary widely, i.e., from less than about 0.5%, usually at least about 1% to as much as 15 or 20% by weight and will be selected primarily based on fluid volumes, viscosities, etc., in accordance with the particular mode of administration selected.

Thus, a typical pharmaceutical composition for injection could be made up to contain 1 ml sterile buffered water, and 1–10 mg of immunoglobulin. A typical composition for intravenous infusion could be made up to contain 250 ml of sterile Ringer's solution, and 150 mg of immunoglobulin. Actual methods for preparing parenterally administrable compositions will be known or apparent to those skilled in the art and are described in more detail in, for example, *Remington's Pharmaceutical Science*, 15th ed., Mack Publishing Company, Easton, Pa. (1980), which is incorporated herein by reference.

The immunoglobulins of this invention can be frozen or lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of immunoglobulin activity loss (e.g., with conventional immune globulins, IgM antibodies tend to have greater activity loss than IgG antibodies) and that use levels may have to be adjusted to compensate.

The compositions containing the present humanized immunoglobulins or a cocktail thereof can be administered for therapeutic or prophylactic treatments. In therapeutic application, compositions are administered to a patient already suffering from an arterial thrombosis or other platelet-mediated disease, in an amount sufficient to cure or at least partially arrest the disease and its complications. An amount adequate to accomplish this is defined as a "therapeutically effective dose." Amounts effective for this use will depend upon the severity of the disease and the general state of the patient's own immune system, but generally range from about 1 to about 200 mg of immunoglobulin per dose, with dosages of from 5 to 25 mg per patient being more commonly used. It must be kept in mind that the materials of this invention may generally be employed in serious disease states, that is life-threatening or potentially life-threatening situations. In such cases, in view of the minimization of extraneous substances and the lower probability of "foreign substance" rejections which are achieved by the present humanized immunoglobulins of this invention, it is possible and may be felt desirable by the treating physician to administer substantial excesses of these immunoglobulins. Typical prophylactic uses are treatment of a patient undergoing balloon angioplasty to prevent abrupt closure, and of patients who have had one heart attack or stroke to prevent further attacks.

Single or multiple administrations of the compositions can be carried out with dose levels and pattern being selected by the treating physician. In any event, the pharmaceutical formulations should provide a quantity of the immunoglobulin(s) of this invention sufficient to effectively treat the patient.

In particular embodiments, compositions comprising a humanized immunoglobulin of the present invention may be used to diagnose the presence and location of a thrombus in a human patient. For example but not for limitation, the antigenic determinant bound by the mouse antibody C4G1 is present on platelets but is absent or present in reduced amounts on vascular endothelial cells. Thus, a humanized immunoglobulin of the present invention, such as a humanized immunoglobulin that binds to the antigenic determinant identified by the mouse antibody C4G1, may be labeled and used to identify anatomical sites that contain significant concentrations of activated platelets, for example thrombus sites. For example but not for limitation, one or more labeling moieties may be attached to the humanized immunoglobulin. Exemplary labeling moieties include, but are not limited to, radiopaque dyes, radiocontrast agents, fluorescent molecules, spin-labeled molecules, enzymes, or other labeling moieties of diagnostic value, particularly in radiologic or magnetic resonance imaging techniques.

Humanized immunoglobulins of the present invention can further find a wide variety of utilities in vitro. By way of example, the immunoglobulins can be utilized for detection of GPIIb/IIIa antigens, for isolating platelets, or the like.

For diagnostic purposes, the immunoglobulins may either be labeled or unlabeled. Unlabeled immunoglobulins can be used in combination with other labeled antibodies (second antibodies) that are reactive with the humanized immunoglobulin, such as antibodies specific for human immunoglobulin constant regions. Alternatively, the immunoglobulins can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays are available and are well known to those skilled in the art.

Kits can also be supplied for use with the subject immunoglobulins in the protection against or detection of a cellular activity or for the presence of a selected antigen. Thus, the subject immunoglobulin composition of the present invention may be provided, usually in a lyophilized form in a container, either alone or in conjunction with additional antibodies specific for the desired cell type. The immunoglobulins, which may be conjugated to a label or toxin, or unconjugated, are included in the kits with buffers, such as Tris, phosphate, carbonate, etc., stabilizers, preservatives, biocides, biocides, inert proteins, e.g., serum albumin, or the like, and a set of instructions for use. Generally, these materials will be present in less than about 5% wt. based on the amount of active immunoglobulin, and usually present in total amount of at least about 0.001% wt. based again on the immunoglobulin concentration. Frequently, it will be desirable to include an inert extender or excipient to dilute the active ingredients, where the excipient may be present in from about 1 to 99% wt. of the total composition. Where a second antibody capable of binding to the immunoglobulin is employed in an assay, this will usually be present in a separate vial. The second antibody is typically conjugated to a label and formulated in an analogous manner with the immunoglobulin formulations described above.

The following examples are offered by way of illustration, not by limitation. It will be understood that although the examples pertain to the C4G1 antibody, producing humanized antibodies with high binding affinity for the GPIIb/IIIa antigen is also contemplated using CDR's from 10E5, 7E3, AP-2 or other monoclonal antibodies that bind to an epitope of GPIIb/IIIa.

EXPERIMENTAL

Cloning of heavy chain and light chain cDNA cDNAs for the heavy chain and light chain variable domain genes were cloned using anchored polymerase chain reactions (E.Y. Loh et al., Science 243, 217 (1989)), using 3' primers that hybridized to the constant regions and contained HindIII sites, and 5' primers that hybridized to the dG tails and contained EcoRI sites (scheme shown in FIG. 1). The PCR amplified fragments were digested with EcoRI and HindIII and cloned into the pUC18 vector for sequencing. For C4G1, two gamma-1 specific and two kappa specific clones were sequenced. The two gamma-1 clones and two kappa clones are respectively identical in sequence. The cDNA variable domain sequences and the deduced amino acid sequences are shown in FIG. 2.

Construction and expression of chimeric antibody

Two plasmid vectors were prepared for construction and expression of the chimeric antibody genes. The plasmid pVg1-dhfr (FIG. 3A) contains a human cytomegalovirus IE1 promoter and enhancer (M. Boshart et al., Cell 41, 521 (1985)), the human genomic Cγ1 segment including part of the preceding intron, and a dihydrofolate reductase (dhfr) gene (Simonsen et al., Proc. Natl Acad. Sci. USA 80, 2495 (1984), which is incorporated herein by reference) for selection. The plasmid pVk (FIG. 3B) is similar to pVg1-dhfr but contains the human genomic Cκ segment and the gpt gene. Derivatives of the C4G1 heavy and light chain variable regions were prepared from the cDNAs by polymerase chain reaction. The 5' primers hybridized to the V regions starting at the ATG codons and contained XbaI sites; the 3' primers hybridized to the last 15 nucleotides of the J regions and contained splice donor signals and XbaI sites (see, Queen et al., Proc. Natl. Acad. Sci. USA 86, 10029 (1989), which is incorporated herein by reference). The modified V regions were cloned into the XbaI sites of the respective plasmid vectors between the CMV promoter and the partial introns of the constant regions.

Figure 4:
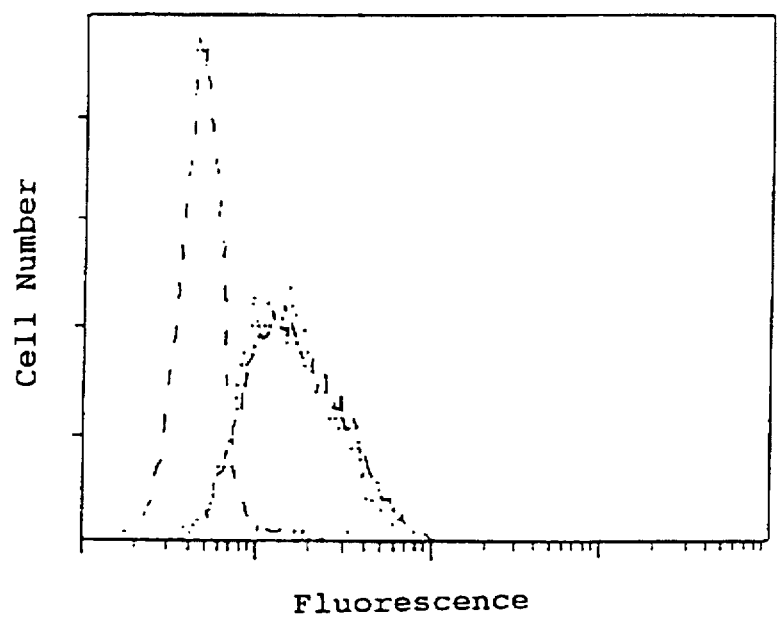
FIG. 4. Flow cytometry analysis of purified chimeric and humanized C4G1 antibody binding to HEL 92.1.7 cells expressing the GPIIb/IIIa antigen.

For expression of the chimeric antibody, the heavy chain and kappa chain plasmids were transfected into Sp2/0 mouse myeloma cells by electroporation and cells selected for gpt expression. Clones secreting a maximal amount of complete antibody were detected by ELISA. Purified chimeric C4G1 antibody was shown to bind to HEL 92.1.7 cells, which express the GPIIb/IIIa antigen, by flow cytometry (FIG. 4).

Computer modeling of humanized antibodies

In order to retain high binding affinity in the humanized antibodies, the general procedures of Queen et al. were followed (see, Queen et al., Proc. Natl. Acad. Sci. USA 86, 10029 (1989) and WO 90/07861, which are incorporated herein by reference). The more homologous a human antibody is to the original murine antibody, the less likely will combining the murine CDR's with the human framework be to introduce distortions into the CDR's that could reduce affinity. Normally the heavy chain and light chain from the same human antibody are chosen to provide the framework sequences, so as to reduce the possibility of incompatibility in the assembling of the two chains. Based on sequence homology search against the NBRF protein sequence database (performed with the MicroGenie Sequence Analysis Software (Beckman)), the antibody Eu was chosen to provide the framework sequences for humanization of C4G1.

The computer program ENCAD (M. Levitt, J. Mol. Biol. 168, 595 (1983), which is incorporated herein by reference) was used to construct a model of the C4G1 variable region. The model was used to determine the amino acids in the C4G1 framework that were close enough to the CDR's to potentially interact with them (category 4 below). To design the humanized light and heavy chain C4G1 variable regions, at each position the amino acid was chosen to be the same as in the Eu antibody, unless that position fell in one or more of five categories:

(1) The position fell within a CDR, (2) The Eu amino acid was unusual for human antibodies at that position, whereas the C4G1 amino acid was typical for human antibodies at that position, (3) The position was immediately adjacent to a CDR, (4) The model described above suggested that the amino acid may be physically close to the antigen binding region (CDR's).

In category (2), "unusual" is interpreted to include amino acids that occur in less than about 20% of the human sequences in the same subgroups (as defined by Kabat et al., op. cit.) as the Eu light and heavy chains, and "typical" is interpreted to include amino acids that occur in more than about 25% but generally more than 50% of the human sequences in those subgroups. For positions in these categories, the amino acid from the mouse C4G1 antibody was used. In addition, a position was in the fifth category if (5) The Eu amino acid was highly unusual for human antibodies at that position, and the G4C1 amino acid was different but also unusual. Then an amino acid typical for human antibodies at that position may be used.

The amino acids in each category are shown in Table 1. Some amino acids may be in more than one category. The final sequences of the humanized C4G1 light and heavy chain variable domains are shown in FIG. 5A and FIG. 5B, compared with the mouse C4G1 sequences.

TABLE 1

| Category | Light Chain | Heavy Chain |
| --- | --- | --- |
| 1 | 24–34, 50–56, 89–97 | 31–35, 50–66, 99–108 |
| 2 | 48, 63 | 93, 98, 109, 110, 113 |
| 3 | — | 30, 98, 109 |
| 4 | 7, 22, 48, 70, 71, 87 | 27, 28, 30, 48, 70, 72, 98, 109 |
| 5 | — | 111 |

Synthesis of humanized antibody

For the construction of genes for the humanized antibodies, nucleotide sequences were selected that encode the protein sequences of the humanized heavy and light chains, including typical immunoglobulin signal peptides, generally utilizing codons found in the mouse sequence. Several degenerate codons were changed to create restriction sites or to remove undesirable ones. The nucleotide sequences also included the same splice donor signals used in the chimeric genes and an XbaI site at each end. Each gene was constructed from four overlapping synthetic oligonucleotides. For each variable domain gene, two pairs of overlapping oligonucleotides on alternating strands were synthesized that encompassed the entire coding sequences as well as the signal peptide and the splice donor signal (FIG. 6). The oligonucleotides were synthesized on an Applied Biosystems 380B DNA synthesizer. Each oligonucleotide was about 110–140 bases long with about a 15 base overlap. Double stranded DNA fragments were synthesized with Klenow polymerase from each pair of oligonucleotides, digested with restriction enzymes, ligated to the pUC18 vector and sequenced. Two fragments with the respectively correct half-sequences were then ligated into the XbaI sites of the pVg1-dhfr or pVk expression vectors in the appropriate orientations to produce the complete heavy and light chain genes. For example, the humanized C4G1 variable domain gene was then contained on an Xba I fragment in pVg1-dhfr. Reactions were carried out under conditions well-known in the art (Maniatis et al., op. cit.). The expected amino acid sequences of the complete light and heavy chains of the humanized C4G1 antibody are shown in FIGS. 5C and 5D.

The heavy chain and light chain plasmids were transfected into Sp2/0 mouse myeloma cells by electroporation and cells were selected for gpt expression. Clones were screened by assaying human antibody production in the culture supernatant by ELISA, and antibody was purified from the best-producing clones. Antibody was purified by passing tissue culture supernatant over a column of staphylococcal protein A-Sepharose CL-4B (Pharmacia). The bound antibody was eluted with 0.2M Glycine-HCl, pH3.0 and neutralized with 1M Tris pH8.0. The buffer was exchanged into PBS by passing over a PD10 column (Pharmacia).

Synthesis of Humanized Fab and F(ab')$_2$ Fragments

Figure 3A:
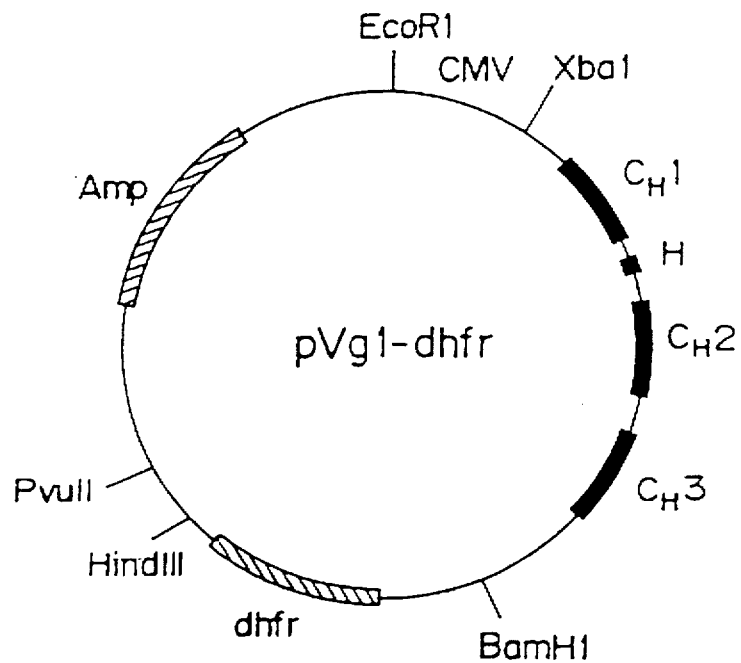
FIGS. 3A and 3B. Schematic diagram of the plasmids pVg1-dhfr (A) and pVk (B). The plasmid pVg1-dhfr contains the following parts: an approximately 4200 base pair BamHI-EcoRI fragment containing the amp and dhfr genes; a 630-bp fragment containing the human cytomegalovirus (CMV) IE1 gene promoter and enhancer (Boshart et al., *Cell* 41, 521 (1985), which is incorporated herein by reference) flanked at the 5' and 3' ends by EcoRI and XbaI linkers respectively; and a 2800 bp HindIII-PvuII fragment containing the human gamma-1 constant region gene with 215 bp of the preceding intron and the poly(A) signal (Ellison et al., *Nucleic Acids Res.* 10, 4071 (1982), which is incorporated herein by reference). The plasmid pVk was similarly constructed, with a 1530-bp EcoRI-XbaI fragment containing the human kappa constant region gene and about 335 bp of the preceding intron (Hieter et al., *Cell* 22, 197 (1980), which is incorporated herein by reference) replacing the gamma-1 gene; and the gpt gene replacing the dhfr gene. The fragments containing the human gamma-1 and kappa constant region genes were flanked at their 5' and 3' ends respectively by created XbaI and BamHI sites. The plasmids were constructed from the indicated parts using methods well-known in the art (see, Maniatis et al., *Molecular Cloning: A Laboratory Manual*, 2nd ed., Cold Spring Harbor Laboratory, Cold Spring Harbor, N.Y.
Figure 3B:
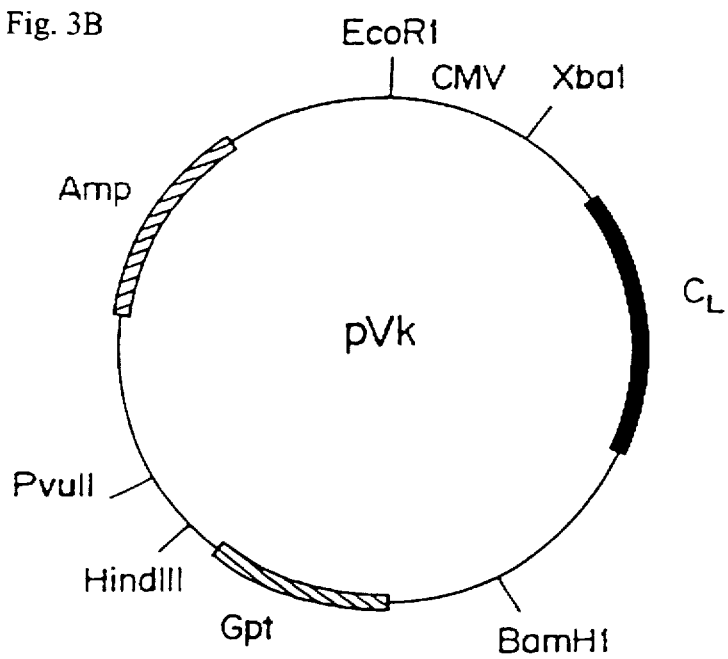
Figure 7A:
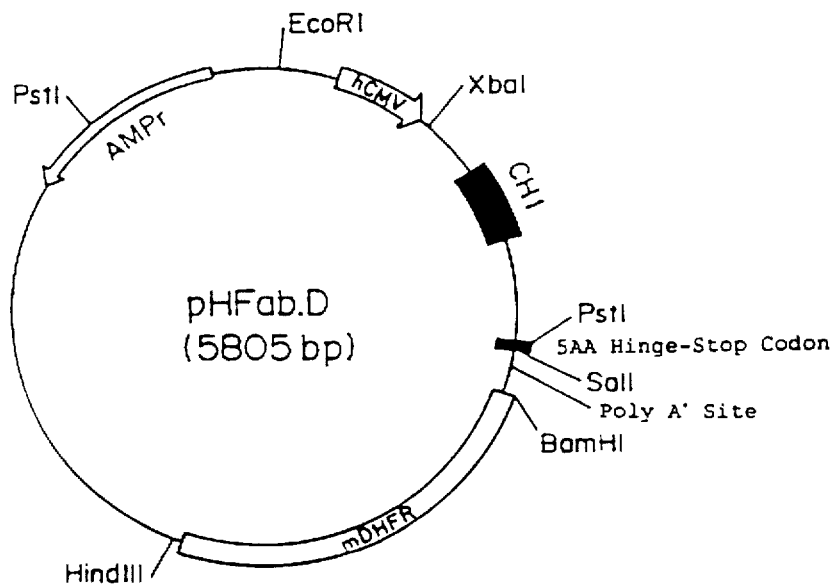
Figure 7B:
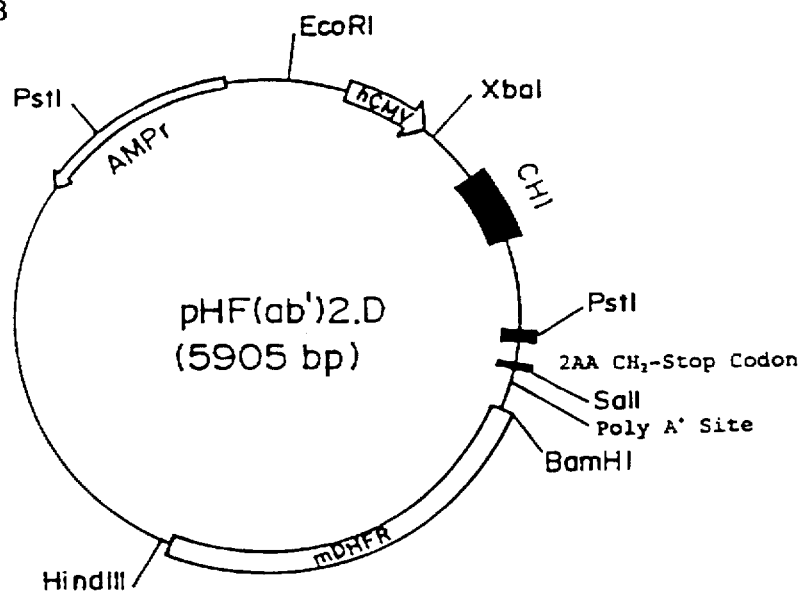

Two additional vectors were constructed in order to synthesize the humanized Fab and F(ab')$_2$ fragments (FIGS. 7A and 7B). To distinguish the recombinant F(ab')$_2$ fragment produced directly using the vector from an F(ab')$_2$ fragment produced by enzymatic cleavage, the recombinant fragment will be designated F(ab')$_2$-1. From the Xba I site counterclockwise to the Bam HI site, these plasmids are the same as pVg1-dhfr (FIG. 3A). However, instead of the complete human $C_{\gamma1}$ gene, the plasmid pHFab.D contains only the $C_H1$ exon and the first 5 amino acids of the hinge exon, followed by a stop codon and splice donor signal, and the plasmid pHF(ab')2.D contains only $C_H1$, the hinge and the first 2 amino acids of $C_H2$ (counting the codon that bridges the splice as part of the hinge), followed by a stop codon and splice donor signal. In both plasmids, the final exon is followed by a 162 bp Sal I - Bam HI fragment, which was taken from the region immediately following the $C_H3$ exon of the mouse γ2a constant region gene and which contains a polyadenylation signal. The Xba I fragment containing the humanized C4G1 heavy chain variable domain gene, described above, was then inserted in the appropriate orientation into the Xba I sites of each of the plasmids pHFab.D and pHF(ab')2.D. All plasmids were constructed by standard methods, including oligonucleotide synthesis and polymerase chain reaction, well known to those skilled in the art of genetic engineering. The expected amino acid sequences of the heavy chains in the humanized C4G1 Fab and F(ab')$_2$-1 fragments are shown in FIGS. 7C and 7D; the light chain in these fragments is the same as in the complete antibody (FIG. 5C).

Each heavy chain containing plasmid was respectively transfected into Sp2/0 cells together with the humanized C4G1 light chain containing plasmid by electroporation, and cells were selected for gpt expression. Clones were screened by assaying for human antibody fragments in the culture supernatants by ELISA, and humanized C4G1 antibody Fab or F(ab')$_2$-1 fragment was purified from the best-producing clones. For each fragment, concentrated culture supernatant was first passed through a DEAE-Sepharose column in 20 mM Tris-Cl, pH 8.6, and the flow-through fraction was used for further purification. The Fab fragment was further purified by chromatography on CM-Sepharose and Phenyl-Sepharose, while the F(ab')$_2$-1 fragment was further purified by chromatography on CM-Sepharose and Phenyl-Sepharose and on S-200, to separate F(ab')$_2$-1 from other oligomers of Fab', using methods well known in the art. Other art-known methods of protein preparation and purification may also be applied. For example, the DEAE-Sepharose flow-through fraction of F(ab')$_2$-1 can be incubated in 10 mM reduced glutathione at pH 9.0 to increase the yield of F(ab')$_2$-1.

The humanized C4G1 antibody and fragments may also be purified in other, slightly or substantially different ways. In each case, the cells are removed from the culture supernatant by centrifugation at 10,000 g for 10 min, the supernatant is filtered using a 0.45 μm filter, and then concentrated about 20-fold using a membrane with molecular weight cut-off (MWCO) of 30,000 for whole antibody and 10,000 for the fragments. For example, to prepare whole humanized C4G1 antibody concentrated culture supernatant was then adjusted to pH 7.5 with 1M Tris, centrifuged at 10,000 g for 10 min and filtered through a 0.45 μm filter. The sample was then loaded on a Protein A-Sepharose FF column (Pharmacia), using 0.15M NaCl, 0.05M Tris, pH 7.5, 2 mM EDTA as the equilibrium and wash buffer. The antibody was eluted with 0.1M acetic acid adjusted to pH 3.5 with Tris base, and the pooled fractions were adjusted to pH 7.5 with Tris. The pool was then dialized against PBS using sterile dialysis tubing and filter sterilized using a 0.2 Mm filter.

To purify the humanized C4G1 Fab fragment for ex vivo experiments in monkeys, the concentrated culture supernatant was diafiltered against 20 mM Tris, pH 8.6, centrifuged at 10,000 g for 10 min and filtered through a 0.45 μm filter. The sample was applied to a DEAE Sepharose (Pharmacia) column equilibrated with 10 mM Tris, pH 8.6, and the flow-through was collected. The DEAE pool was made 10 mM in MES and adjusted to pH 6.5 with HCl. The sample was then applied to a CM Sepharose (Pharmacia) column equilibrated with 10 mM MES, pH 6.5, and eluted with a 0–500 mM NaCl gradient. The Fab fragment was contained in the first peak. The pool of peak fractions was concentrated using a 10,000 MWCO membrane and loaded on a Sephacryl S-200 (Pharmacia) column equilibrated with PBS. The peak fractions were pooled and filter sterilized using a 0.2 µm filter.

The humanized C4G1 F(ab')$_2$-1 fragment can be prepared and purified as follows. The concentrated culture supernatant is diafiltered against 20 mM Tris, pH 8.6, centrifuged at 10,000 g for 10 min and filtered through a 0.45 µm filter. The sample is applied to a DEAE Sepharose (Pharmacia) column equilibrated with 10 mM Tris, pH 8.6, and the flow-through is collected. The DEAE pool is concentrated about 10-fold using 10,000 MWCO membrane and adjusted to pH 5.0 with acetic acid, and the precipitate is removed by centrifugation. The sample is then adjusted to pH 9.0 with Tris, and 10 mM reduced glutathione is added and incubated for 30 min at 22° C. The sample is then dialyzed for 16 hr at 4° C. against 0.1M Tris, pH 9.0, which results in about 30% F(ab')$_2$-1 formation. The sample is then concentrated about 10-fold using a 10,000 MWCO membrane and loaded onto a Sephacryl S-200 column. The 90 kDa peak is collected and filter sterilized using a 0.2 µm filter.

Cell lines that produce higher levels of the humanized C4G1 antibody and fragments are obtained by incubating producing cell lines in increasing concentrations of methotrexate (Simonsen et al., op. cit.). Alternatively, Fab and F(ab')$_2$ fragments can be prepared by enzymatic cleavage of intact humanized C4G1 antibody using methods well known in the art (*Antibodies. A Laboratory Manual*, Harlow and Lane, eds., Cold Spring Harbor Laboratory, 1988, which is incorporated herein by reference), instead of by recombinant methods as above.

For example, another form of the humanized C4G1 F(ab')$_2$ fragment, designated F(ab')$_2$-2, was prepared by pepsin digestion as follows. The culture supernatant of the humanized C4G1 IgG producing cells was adjusted to pH 8.5 with 1M Tris, and applied to a protein A affinity membrane device (Nygene) equilibrated with 50 mM Tris pH 8.5, 150 mM NaCl, 2 mM EDTA. The whole antibody was eluted with 0.1M Glycine-HCl pH 2.5, and the pooled fractions were adjusted to pH 3.5 with 1M Tris. Thus prepared IgG was digested by pepsin from Porcine Stomach Mucosa (Sigma). The pepsin was dissolved in 0.1M Glycine-HCl pH 3.5 and added to the IgG solution (the enzyme: IgG ratio (w/w) should be 1:100). The reaction mixture was incubated with inverting for 3 hrs. at 37° C., and the reaction was stopped by addition of 1M Tris to adjust to pH 8.0. The pepsin digested fraction was then adjusted to 0.75M (NH$_4$)$_2$SO$_4$, and applied to a Phenyl-5PW (Tosoh) column equilibrated with 50 mM CH$_3$COONa pH 6.0, 0.75M (NH$_4$)$_2$SO$_4$. The sample was eluted with a linear gradient from 0.75M to 0M (NH$_4$)$_2$SO$_4$. The F(ab')$_2$-2 was contained in the main peak.

Properties of humanized antibodies

The humanized C4G1 antibody was characterized in comparison to the murine and chimeric antibodies. The humanized antibody bound to HEL 92.1.7 cells in a fluorocytometric analysis in a manner similar to the chimeric antibody (FIG. 4), showing that it recognizes the GPIIb/IIIa antigen.

Purified humanized C4G1 antibody, Fab fragment, F(ab')$_2$-1 fragment and F(ab')$_2$-2 fragment were reduced and run on an SDS-PAGE gel. The whole antibody showed 2 bands of approximate molecular weights 25 kDa and 50 kDa, and the Fab and F(ab')$_2$-1 fragments showed a doublet of bands of approximately 25 kDa. The humanized C4G1 F(ab')$_2$-2 fragment showed the same mobility as the F(ab')$_2$-1 fragment on SDS-PAGE. These results are consistent with the molecular weights of the light chain and heavy chain or heavy chain fragment calculated from their amino acid compositions.

Figure 8A:
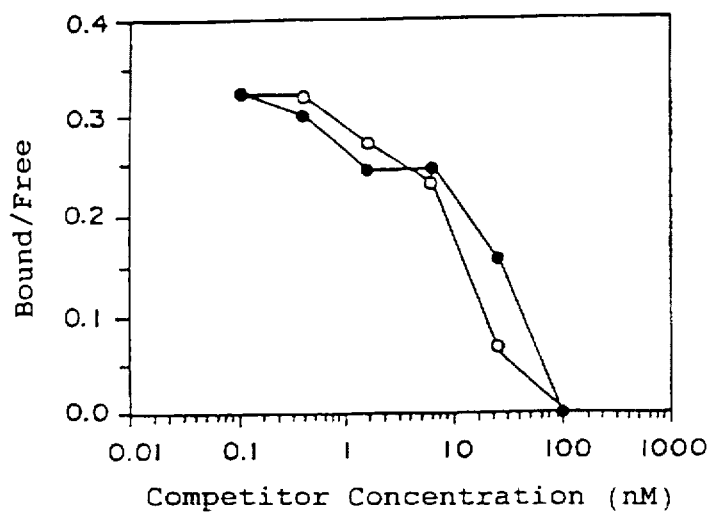
FIGS. 8A, B and C. Competitive binding of humanized and mouse C4G1 antibodies and fragments to platelets. About $3 \times 10^7$ platelets were incubated with 4.5 ng of radio-iodinated mouse C4G1 tracer antibody (3.5 µCi/µg) and varying amounts of either unlabeled mouse C4G1 antibody or fragments (closed symbols) or humanized C4G1 antibody or fragments (open symbols). (A) Intact antibodies. (B) Fab fragments. (C) Mouse F(ab')₂ and humanized F(ab')₂-1 fragments.
Figure 8B:
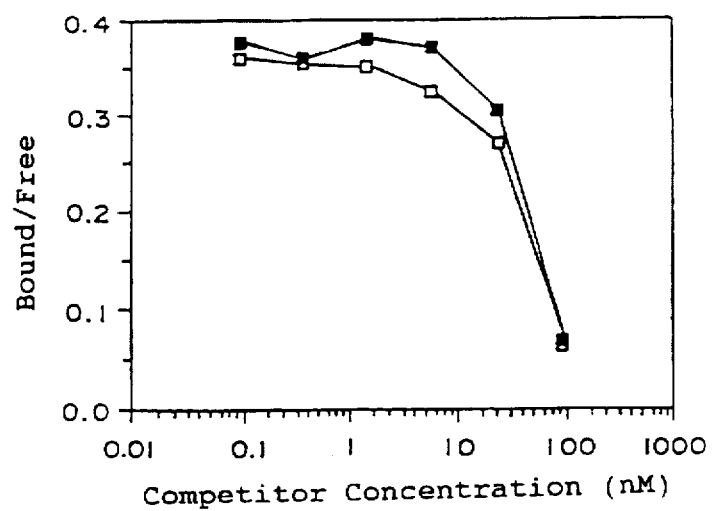
Figure 8C:
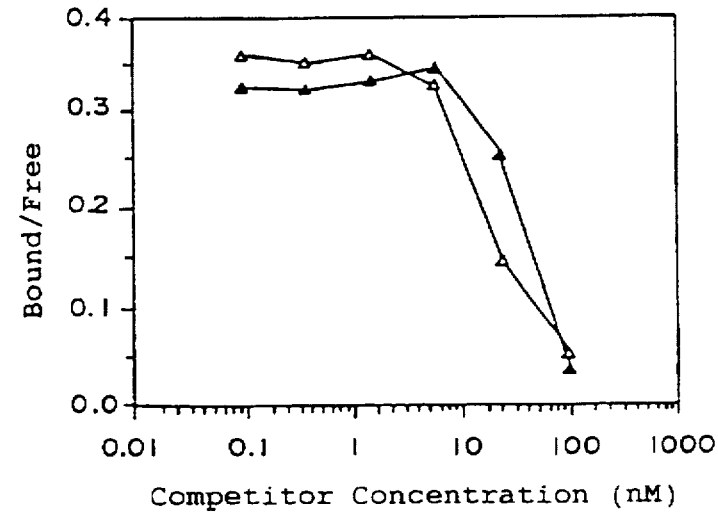

The affinities of the humanized C4G1 antibody, Fab fragment and F(ab')$_2$-1 fragment were determined by competitive binding with the respective mouse C4G1 antibody and fragments. Purified human platelets were used as source of the GPIIb/IIIa antigen. The platelets were purified from buffy coats from normal human donors by centrifugation on ficoll-hypaque. Increasing amounts of humanized or mouse competitor antibody or fragment was added to 4.5 ng of radioiodinated tracer C4G1 antibody (3.5 µCi/ug) and incubated with 3×10$^7$ platelets in 0.2 ml of modified Tyrode's buffer for 1 hr. at room temperature. Cells were washed with 2 ml of ice-cold buffer and pelleted. The radioactivities were measured, and the concentrations of bound and free tracer antibody were calculated (FIG. 8). The binding affinities of the various antibodies and fragments were calculated as in Queen et al., Proc. Nat. Acad. Sci. USA 86, 10029 (1989). The results clearly show that there is no significant difference in binding affinities between respectively the humanized and mouse C4G1 antibodies (FIG. 8A), the humanized and mouse C4G1 Fab fragments (FIG. 8B), and the humanized and mouse C4G1 (Fab')$_2$ fragments (FIG. 8C). The same result was obtained when competitive binding was performed with HEL 92.1.7 cells as source of GPIIb/IIIa antigen. Moreover all the actual binding affinities to these cells were about 10$^8$ M$^{-1}$ or higher.

Figure 9A:
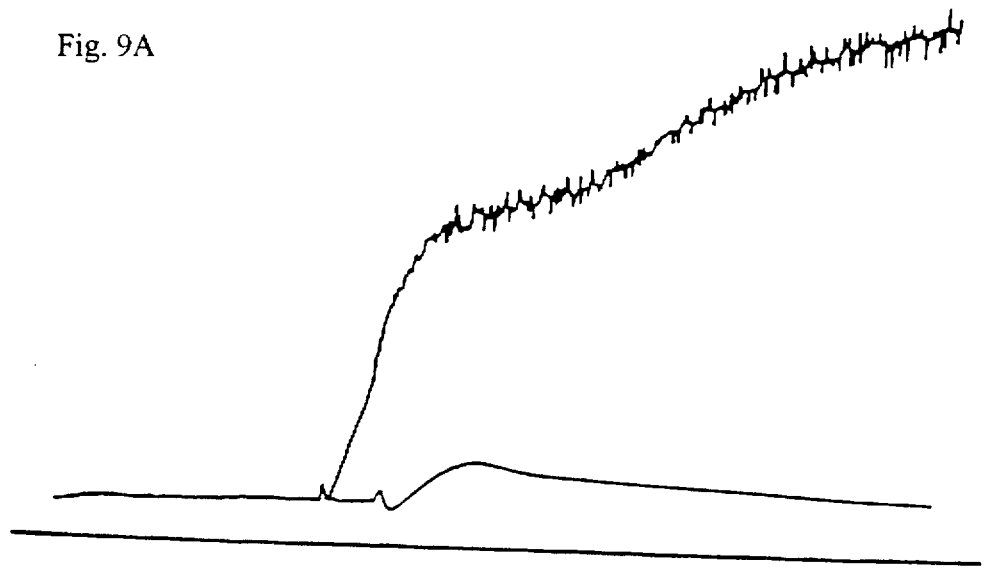
FIGS. 9A and 9B. Inhibition of platelet aggregation by mouse (A) and humanized (B) C4G1 antibodies. The Y-axis shows percent light transmission; the X-axis shows time in minutes. The dark upper curve in each panel shows the increase in light transmission caused by platelet aggregation when no antibody is added; the lighter lower curves show that addition of antibodies strongly inhibits platelet aggregation. as measured by change in light transmission.
Figure 9B:
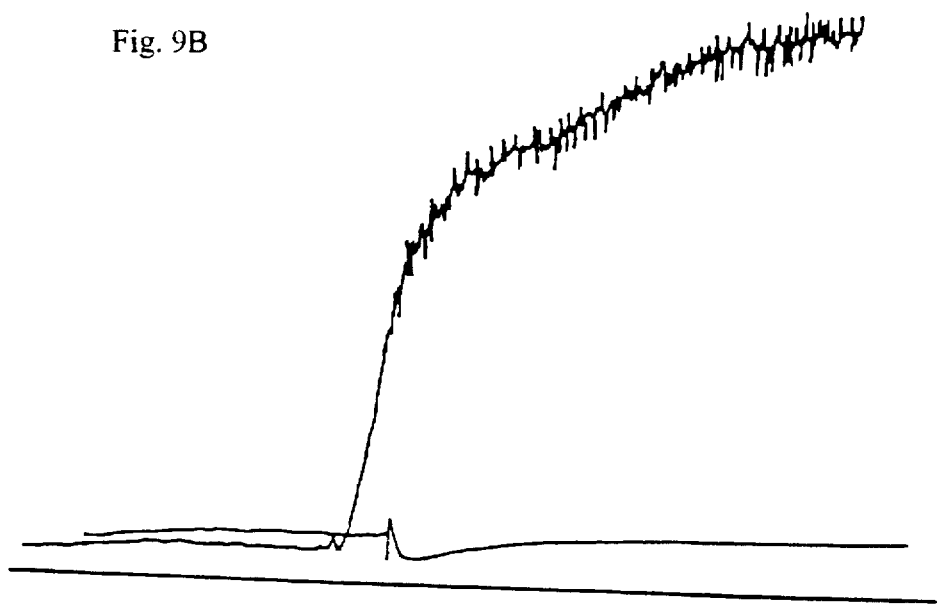

The ability of the mouse and humanized C4G1 antibodies and fragments to inhibit platelet aggregation was determined. Each antibody or fragment was added to platelet rich plasma, prepared by centrifuging freshly drawn citrated blood at 200×g for 10 min., at a final concentration of 5 µg/ml and incubated for 5 min. with stirring at 37° C. ADP was added to a final concentration of 4.6 µM to initiate aggregation. Platelet aggregation was monitored by light transmission, using a Sienco dual sample aggregation meter, model DP-247F or HEMA-TRACER. There were no significant differences in the ability of the humanized and mouse C4G1 antibody to inhibit aggregation (FIG. 9) or of the respective humanized and mouse Fab and (Fab')$_2$-1 fragments to inhibit aggregation. And there were no significant differences in the ability of the humanized C4G1 F(ab')$_2$-1 and F(ab')$_2$-2 fragments to inhibit aggregation.

Binding of the murine and the humanized C4G1 antibodies to human umberical vein endothelial cells (HUVEC) was examined in comparison with binding of a murine monoclonal antibody B6A3, which is specific to GPIIIa. Recent evidence indicates that the receptor present on endothelial cells is probably not authentic GPIIb/IIIa, but rather the vitronectin receptor, which is composed of a protein homologous to, but clearly different from GPIIb, and a protein probably identical in primary structure to GPIIIa (Coller et al., (1989) Circulation 80:1766–73). Binding of the antibodies to HEL 92.1.7. cells was also examined. The antibodies were radiolabeled (3.5 µCi/gg) as described above. Suspensions of 500 µl HUVEC or HEL 92.1.7. (2×10$^4$/ml, 2×10$^5$/ml, 2×10$^6$/ml) were incubated for 90 min with 100 fmole of each monoclonal antibody at room temperature or at 4° C. in 1.5 ml Eppendorf tubes. After incubation the tube contents were layered onto silicone oil in Eppendorf centrifuge tubes and spun at 10,000×g for 2 min at room temperature. The pellet and supernatant were counted separately in a gamma counter. Nonspecific binding was measured at a 100-fold excess of unlabeled antibody and subtracted from the total bound to give specific binding. Both the murine and the humanized C4G1 monoclonal antibodies showed specific binding to HEL 92.1.7. cells as well as the murine B6A3 at the cell density $2\times10^5$/ml and $2\times10^6$/ml. In contrast, neither the murine C4G1 nor the humanized C4G1 showed specific binding to HUVEC at any cell densities whereas the murine B6A3 bound specifically to HUVEC at $2\times10^6$/ml. These results indicate that the epitope recognized by the murine C4G1 immunoglobulin and its humanized derivative is absence, or present only in reduced amounts (such that no specific binding was observed under the present conditions), on vascular endothelial cells.

Ex vivo inhibitory activity of ADP-induced platelet aggregation

The ability of the humanized C4G1 Fab and $F(ab')_2$ fragments to inhibit ex vivo platelet aggregation from monkeys was determined. Although platelets from all healthy human volunteers responded to humanized C4G1, the platelets from some rhesus monkeys did not respond to humanized C4G1. Therefore, only rhesus monkeys with platelets responding to humanized C4G1 were chosen for this experiment.

Each fragment was suspended in 5 ml saline solution and administered I.V. to rhesus monkeys (male, 2.8–5.0 kg weight). In the placebo control, 5 ml saline solution was administered. Blood was collected 1 hr after administration under anesthesia with ketamine hydrochloride, and immediately citrated and centrifuged at 200 g for 10 min. The supernatant was used as platelet-rich plasma. Platelet-poor plasma was prepared from the remaining blood after platelet-rich plasma was removed by centrifuging the blood at 2000 g. Platelet-rich plasma was diluted with platelet-poor plasma to achieve a platelet count of $3\times10^8$/ml.

ADP was added to a final concentration of 20 µM to initiate aggregation. Platelet aggregation was monitored by light transmission.

Platelet aggregation was completely inhibited in the platelets obtained from monkeys treated with the humanized C4G1 Fab and $F(ab')_2$-1 fragments. The $F(ab')_2$-1 fragment completely inhibited platelet aggregation at a dose of 0.5 mg/kg body weight. Treatment with the fragments did not cause significant thrombocytopenia in the monkeys.

From the foregoing, it will be appreciated that the humanized immunoglobulins of the present invention offer numerous advantages over other GPIIb/IIIa specific antibodies. In comparison to mouse monoclonal antibodies, the present humanized immunoglobulins contain substantially less foreign amino acid sequences. This reduced likelihood of antigenicity after injection into a human patient represents a significant therapeutic improvement.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

We claim:

1. A humanized immunoglobulin which specifically binds to GPIIb/IIIa comprising:
   a humanized light chain comprising three complementarity determining regions from the mouse C4G1 antibody and a light chain variable region framework sequence from a human immunoglobulin light chain, and
   a humanized heavy chain comprising three complementarity determining regions from the mouse C4G1 antibody and a heavy chain variable region framework sequence from a human immunoglobulin heavy chain,
   wherein the mouse C4G1 antibody has a mature light chain variable domain designated SEQ. ID. No. 9, and a mature heavy chain variable domain designated SEQ. ID. No. 11.

2. The humanized immunoglobulin of claim 1, having a mature light chain variable region sequence as shown in SEQ. ID NO:8, and a mature heavy chain variable region sequence as shown in SEQ. ID NO:10.

3. A humanized immunoglobulin according to claim 2, wherein the immunoglobulin is an Fab or F(ab')$_2$.

4. A humanized immunoglobulin according to claim 2, having a light chain sequence as shown in SEQ. ID NO:12, and a heavy chain sequence as shown in SEQ. ID NO:13.

5. A humanized immunoglobulin obtainable by enzymatic cleavage of a humanized immunoglobulin according to claim 2.

6. A humanized immunoglobulin according to claim 5, wherein the immunoglobulin is an F(ab')$_2$.

7. A humanized immunoglobulin according to claim 5, wherein the immunoglobulin is an Fab.

8. A humanized immunoglobulin according to claim 2, wherein the immunoglobulin is an IgG$_1$ immunoglobulin isotype.

9. A humanized immunoglobulin according to claim 2 which inhibits the aggregation of human platelets in response to agonists.

10. An immunoglobulin according to claim 2 which was produced in a myeloma cell.

11. A polynucleotide, comprising a sequence coding for a mature light chain variable sequence as shown in SEQ. ID NO:8 or a sequence coding for a mature heavy chain variable sequence as shown in SEQ. ID NO:10.

12. A polynucleotide 11, comprising a sequence coding for a mature light chain as shown in SEQ. ID NO:12 or a sequence coding for a mature heavy chain as shown in SEQ. ID NO:13.

13. An expression vector comprising the polynucleotide sequence of claim 11.

14. An expression vector 13, comprising a polynucleotide of claim 12.

15. A cell line transfected with an expression vector of claim 13.

16. A cell line transfected with expression vectors of claim 13, wherein a first vector comprises the sequence coding for the mature light chain and a second vector comprises the sequence coding for the mature heavy chain.

17. A cell line according to claim 16, wherein a first vector comprises a sequence coding for a protein sequence as shown in SEQ. ID NO:12 and a second vector comprises a sequence coding for a protein sequence as shown in SEQ. ID NO:13.

* * * * *

UNITED STATES PATENT AND TRADEMARK OFFICE
CERTIFICATE OF CORRECTION

PATENT NO. : 5,777,085
DATED : July 7, 1998
INVENTOR(S) : Co et al.

It is certified that error appears in the above-identified patent and that said Letters Patent is hereby corrected as shown below:

In the cover page, item [30] Assignee, please add <u>Yamanouchi Pharmaceuticals Co. Ltd., Tokyo, Japan</u> as a co-assignee as shown below..

Assignees:

Protein Design Labs, Inc.
Mountain View, California

Yamanouchi Pharmaceuticals Co, Ltd.,
Tokyo, Japan

Signed and Sealed this

Twenty-ninth Day of June, 1999

*Attest:*

Q. TODD DICKINSON

*Attesting Officer*    Acting Commissioner of Patents and Trademarks

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: synthetic DNA ( x i ) SEQUENCE DESCRIPTION: SEQ ID NO:1:

```
TAATCTAGAA TTCCCCCCCC CCCCCCCC                                    29
```

( 2 ) INFORMATION FOR SEQ ID NO:2:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: synthetic DNA ( x i ) SEQUENCE DESCRIPTION: SEQ ID NO:2:

```
TATAGAGCTC AAGCTTGGAT GGTGGGAAGA TGGATACAGT TGGTGC              46
```

( 2 ) INFORMATION FOR SEQ ID NO:3:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: synthetic DNA ( x i ) SEQUENCE DESCRIPTION: SEQ ID NO:3:

```
TATAGAGCTC AAGCTTCCAG TGGATAGACH GATGGGGSTG TYGTTTTGGC          50
```

( 2 ) INFORMATION FOR SEQ ID NO:4:

( i ) SEQUENCE CHARACTERISTICS:
        ( A ) LENGTH: 381 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..381

( x i ) SEQUENCE DESCRIPTION: SEQ ID NO:4:

```
ATG ATG TCC TCT GCT CAG TTC CTT GGT TTC CTG TTG CTC TGT TTT CAA          48
Met Met Ser Ser Ala Gln Phe Leu Gly Phe Leu Leu Leu Cys Phe Gln
 1               5                  10                  15

GGT ACC AGA TGT GAT ATC CAG ATG ACA CAG ACT ACA TCC TCC CTG TCT          96
Gly Thr Arg Cys Asp Ile Gln Met Thr Gln Thr Thr Ser Ser Leu Ser
             20                  25                  30

GCC TCT CTG GGA GAC AGA GTC ACC ATC AGT TGC AGG GCA AGT CAG GAC         144
Ala Ser Leu Gly Asp Arg Val Thr Ile Ser Cys Arg Ala Ser Gln Asp
         35                  40                  45

ATT AAC AAT TAT TTA AAC TGG TAT CAG CAG AAA CCA GAT GGA ATT GTT         192
Ile Asn Asn Tyr Leu Asn Trp Tyr Gln Gln Lys Pro Asp Gly Ile Val
     50                  55                  60

AAA CTC CTG ATC TAC TAC ACA TCA ACA TTA CAC TCA GGA GTC CCA TCA         240
Lys Leu Leu Ile Tyr Tyr Thr Ser Thr Leu His Ser Gly Val Pro Ser
 65                  70                  75                  80

AGG TTC AGT GGC AGT GGG TCT GGA ACA GAT TAT TCT CTC ACC ATT AGC         288
Arg Phe Ser Gly Ser Gly Ser Gly Thr Asp Tyr Ser Leu Thr Ile Ser
                 85                  90                  95

AAC CTG GAG CAG GAA GAT ATT GCC ACT TAC TTT TGC CAA CAG GGT AAT         336
Asn Leu Glu Gln Glu Asp Ile Ala Thr Tyr Phe Cys Gln Gln Gly Asn
             100                 105                 110

ACG CTT CCG TGG ACG TTC GGT GGA GGC ACC AAG CTG GAA ATC AAA         381
    Thr Leu Pro Trp Thr Phe Gly Gly Gly Thr Lys Leu Glu Ile Lys
             115                 120                 125
```

( 2 ) INFORMATION FOR SEQ ID NO:5:

( i ) SEQUENCE CHARACTERISTICS:
        ( A ) LENGTH: 127 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Met Ser Ser Ala Gln Phe Leu Gly Phe Leu Leu Leu Cys Phe Gln
 1               5                  10                  15

Gly Thr Arg Cys Asp Ile Gln Met Thr Gln Thr Thr Ser Ser Leu Ser
```

|    |    |    |    |    | 20  |    |    |    |    | 25  |    |    |    |    | 30  |    |
|----|----|----|----|----|-----|----|----|----|----|-----|----|----|----|----|-----|----|
| Ala | Ser | Leu | Gly | Asp | Arg | Val | Thr | Ile | Ser | Cys | Arg | Ala | Ser | Gln | Asp |
|     |     | 35  |     |     |     | 40  |     |     |     |     | 45  |     |     |     |     |

| Ile | Asn | Asn | Tyr | Leu | Asn | Trp | Tyr | Gln | Gln | Lys | Pro | Asp | Gly | Ile | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Lys | Leu | Leu | Ile | Tyr | Tyr | Thr | Ser | Thr | Leu | His | Ser | Gly | Val | Pro | Ser |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Arg | Phe | Ser | Gly | Ser | Gly | Ser | Gly | Thr | Asp | Tyr | Ser | Leu | Thr | Ile | Ser |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asn | Leu | Glu | Gln | Glu | Asp | Ile | Ala | Thr | Tyr | Phe | Cys | Gln | Gln | Gly | Asn |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Thr | Leu | Pro | Trp | Thr | Phe | Gly | Gly | Gly | Thr | Lys | Leu | Glu | Ile | Lys |
|-----|-----|-----|-----|-----|-----|-----|-----|-----|-----|-----|-----|-----|-----|-----|
|     |     | 115 |     |     |     |     | 120 |     |     |     |     | 125 |     |     |

( 2 ) INFORMATION FOR SEQ ID NO:6:

( i ) SEQUENCE CHARACTERISTICS:
        ( A ) LENGTH: 414 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..414

( x i ) SEQUENCE DESCRIPTION: SEQ ID NO:6:

| ATG | GAA | TGG | AGC | GGA | GTC | TTT | ATC | TTT | CTT | CTG | TCA | GTG | ACT | GCA | AGT | 48 |
|-----|-----|-----|-----|-----|-----|-----|-----|-----|-----|-----|-----|-----|-----|-----|-----|----|
| Met | Glu | Trp | Ser | Gly | Val | Phe | Ile | Phe | Leu | Leu | Ser | Val | Thr | Ala | Ser |    |
| 1   |     |     |     | 5   |     |     |     |     | 10  |     |     |     |     | 15  |     |    |

| GTT | CAC | TCC | CAG | GTC | CAG | CTG | CAG | CAG | TCT | GGA | GCT | GAG | CTG | GTA | GGG | 96 |
|-----|-----|-----|-----|-----|-----|-----|-----|-----|-----|-----|-----|-----|-----|-----|-----|----|
| Val | His | Ser | Gln | Val | Gln | Leu | Gln | Gln | Ser | Gly | Ala | Glu | Leu | Val | Gly |    |
|     |     |     | 20  |     |     |     |     | 25  |     |     |     |     | 30  |     |     |    |

| CCT | GGG | ACT | TCA | GTG | AGG | GTG | TCC | TGC | AAG | GCT | TCT | GGA | TAC | GCC | TTC | 144 |
|-----|-----|-----|-----|-----|-----|-----|-----|-----|-----|-----|-----|-----|-----|-----|-----|-----|
| Pro | Gly | Thr | Ser | Val | Arg | Val | Ser | Cys | Lys | Ala | Ser | Gly | Tyr | Ala | Phe |     |
|     |     | 35  |     |     |     |     | 40  |     |     |     |     | 45  |     |     |     |     |

| ACT | AAT | TAC | TTG | ATA | GAG | TGG | GTA | AAG | CAG | AGG | CCT | GGA | CAG | GGC | CTT | 192 |
|-----|-----|-----|-----|-----|-----|-----|-----|-----|-----|-----|-----|-----|-----|-----|-----|-----|
| Thr | Asn | Tyr | Leu | Ile | Glu | Trp | Val | Lys | Gln | Arg | Pro | Gly | Gln | Gly | Leu |     |
|     | 50  |     |     |     |     | 55  |     |     |     |     | 60  |     |     |     |     |     |

| GAG | TGG | ATT | GGA | GTG | ATT | TAT | CCT | GGA | AGT | GGT | GGT | ACT | AAC | TAC | AAT | 240 |
|-----|-----|-----|-----|-----|-----|-----|-----|-----|-----|-----|-----|-----|-----|-----|-----|-----|
| Glu | Trp | Ile | Gly | Val | Ile | Tyr | Pro | Gly | Ser | Gly | Gly | Thr | Asn | Tyr | Asn |     |
| 65  |     |     |     |     | 70  |     |     |     |     | 75  |     |     |     |     | 80  |     |

| GAG | AAG | TTC | AAG | GGC | AAG | GCA | ACT | CTG | ACT | GTA | GAC | AAA | TCC | TCC | ACC | 288 |
|-----|-----|-----|-----|-----|-----|-----|-----|-----|-----|-----|-----|-----|-----|-----|-----|-----|
| Glu | Lys | Phe | Lys | Gly | Lys | Ala | Thr | Leu | Thr | Val | Asp | Lys | Ser | Ser | Thr |     |
|     |     |     |     | 85  |     |     |     |     | 90  |     |     |     |     | 95  |     |     |

| ACT | GCC | TAC | ATG | CAA | CTC | AGC | AGC | CTG | ACA | TCT | GAT | GAC | TCT | GCG | GTC | 336 |
|-----|-----|-----|-----|-----|-----|-----|-----|-----|-----|-----|-----|-----|-----|-----|-----|-----|
| Thr | Ala | Tyr | Met | Gln | Leu | Ser | Ser | Leu | Thr | Ser | Asp | Asp | Ser | Ala | Val |     |
|     |     |     | 100 |     |     |     |     | 105 |     |     |     |     | 110 |     |     |     |

| TAT | TTC | TGT | GCA | AGA | CGA | GAT | GGT | AAC | TAC | GGA | TGG | TTT | GCC | TAC | TGG | 384 |
|-----|-----|-----|-----|-----|-----|-----|-----|-----|-----|-----|-----|-----|-----|-----|-----|-----|
| Tyr | Phe | Cys | Ala | Arg | Arg | Asp | Gly | Asn | Tyr | Gly | Trp | Phe | Ala | Tyr | Trp |     |
|     |     | 115 |     |     |     |     | 120 |     |     |     |     | 125 |     |     |     |     |

| GGC | CGG | GGG | ACT | CTG | GTC | ACT | GTC | TCT | GCA | 414 |
|-----|-----|-----|-----|-----|-----|-----|-----|-----|-----|-----|
| Gly | Arg | Gly | Thr | Leu | Val | Thr | Val | Ser | Ala |     |
|     | 130 |     |     |     |     | 135 |     |     |     |     |

( 2 ) INFORMATION FOR SEQ ID NO:7:

( i ) SEQUENCE CHARACTERISTICS:
        ( A ) LENGTH: 138 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| Met | Glu | Trp | Ser | Gly | Val | Phe | Ile | Phe | Leu | Leu | Ser | Val | Thr | Ala | Ser |
|---|---|---|---|---|---|---|---|---|---|---|---|---|---|---|---|
| 1 | | | | 5 | | | | | 10 | | | | | 15 | |

| Val | His | Ser | Gln | Val | Gln | Leu | Gln | Gln | Ser | Gly | Ala | Glu | Leu | Val | Gly |
|---|---|---|---|---|---|---|---|---|---|---|---|---|---|---|---|
| | | | 20 | | | | | 25 | | | | | 30 | | |

| Pro | Gly | Thr | Ser | Val | Arg | Val | Ser | Cys | Lys | Ala | Ser | Gly | Tyr | Ala | Phe |
|---|---|---|---|---|---|---|---|---|---|---|---|---|---|---|---|
| | | 35 | | | | | 40 | | | | | 45 | | | |

| Thr | Asn | Tyr | Leu | Ile | Glu | Trp | Val | Lys | Gln | Arg | Pro | Gly | Gln | Gly | Leu |
|---|---|---|---|---|---|---|---|---|---|---|---|---|---|---|---|
| | 50 | | | | | 55 | | | | | 60 | | | | |

| Glu | Trp | Ile | Gly | Val | Ile | Tyr | Pro | Gly | Ser | Gly | Gly | Thr | Asn | Tyr | Asn |
|---|---|---|---|---|---|---|---|---|---|---|---|---|---|---|---|
| 65 | | | | | 70 | | | | | 75 | | | | | 80 |

| Glu | Lys | Phe | Lys | Gly | Lys | Ala | Thr | Leu | Thr | Val | Asp | Lys | Ser | Ser | Thr |
|---|---|---|---|---|---|---|---|---|---|---|---|---|---|---|---|
| | | | | 85 | | | | | 90 | | | | | 95 | |

| Thr | Ala | Tyr | Met | Gln | Leu | Ser | Ser | Leu | Thr | Ser | Asp | Asp | Ser | Ala | Val |
|---|---|---|---|---|---|---|---|---|---|---|---|---|---|---|---|
| | | | 100 | | | | | 105 | | | | | 110 | | |

| Tyr | Phe | Cys | Ala | Arg | Arg | Asp | Gly | Asn | Tyr | Gly | Trp | Phe | Ala | Tyr | Trp |
|---|---|---|---|---|---|---|---|---|---|---|---|---|---|---|---|
| | | 115 | | | | | 120 | | | | | 125 | | | |

| Gly | Arg | Gly | Thr | Leu | Val | Thr | Val | Ser | Ala |
|---|---|---|---|---|---|---|---|---|---|
| | 130 | | | | | 135 | | | |

( 2 ) INFORMATION FOR SEQ ID NO:8:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Asp | Ile | Gln | Met | Thr | Gln | Thr | Pro | Ser | Thr | Leu | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Ser | Cys | Arg | Ala | Ser | Gln | Asp | Ile | Asn | Asn | Tyr |
|---|---|---|---|---|---|---|---|---|---|---|---|---|---|---|---|
| | | | 20 | | | | | 25 | | | | | 30 | | |

| Leu | Asn | Trp | Tyr | Gln | Gln | Lys | Pro | Gly | Lys | Ala | Pro | Lys | Leu | Leu | Ile |
|---|---|---|---|---|---|---|---|---|---|---|---|---|---|---|---|
| | | | 35 | | | | | 40 | | | | | 45 | | |

| Tyr | Tyr | Thr | Ser | Thr | Leu | His | Ser | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Tyr | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Asp | Asp | Phe | Ala | Thr | Tyr | Phe | Cys | Gln | Gln | Gly | Asn | Thr | Leu | Pro | Trp |
|---|---|---|---|---|---|---|---|---|---|---|---|---|---|---|---|
| | | | | 85 | | | | | 90 | | | | | 95 | |

| Thr | Phe | Gly | Gln | Gly | Thr | Lys | Val | Glu | Val | Lys |
|---|---|---|---|---|---|---|---|---|---|---|
| | | | 100 | | | | | 105 | | |

( 2 ) INFORMATION FOR SEQ ID NO:9:

( i ) SEQUENCE CHARACTERISTICS:
        ( A ) LENGTH: 107 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

| Asp | Ile | Gln | Met | Thr | Gln | Thr | Thr | Ser | Ser | Leu | Ser | Ala | Ser | Leu | Gly |
|---|---|---|---|---|---|---|---|---|---|---|---|---|---|---|---|
| 1 | | | | 5 | | | | | 10 | | | | | 15 | |

```
Asp Arg Val Thr Ile Ser Cys Arg Ala Ser Gln Asp Ile Asn Asn Tyr
            20              25              30

Leu Asn Trp Tyr Gln Gln Lys Pro Asp Gly Ile Val Lys Leu Leu Ile
        35              40              45

Tyr Tyr Thr Ser Thr Leu His Ser Gly Val Pro Ser Arg Phe Ser Gly
    50              55              60

Ser Gly Ser Gly Thr Asp Tyr Ser Leu Thr Ile Ser Asn Leu Glu Gln
65              70              75              80

Glu Asp Ile Ala Thr Tyr Phe Cys Gln Gln Gly Asn Thr Leu Pro Trp
            85              90              95

Thr Phe Gly Gly Gly Thr Lys Leu Glu Ile Lys
            100             105
```

( 2 ) INFORMATION FOR SEQ ID NO:10:

( i ) SEQUENCE CHARACTERISTICS:
      ( A ) LENGTH: 119 amino acids
      ( B ) TYPE: amino acid
      ( D ) TOPOLOGY: linear ( i i ) MOLECULE TYPE: protein ( v ) FRAGMENT TYPE: N-terminal fragment ( x i ) SEQUENCE DESCRIPTION: SEQ ID NO:10:

```
Gln Val Gln Leu Val Gln Ser Gly Ala Glu Val Lys Lys Pro Gly Ser
 1               5              10              15

Ser Val Lys Val Ser Cys Lys Ala Ser Gly Tyr Ala Phe Thr Asn Tyr
            20              25              30

Leu Ile Glu Trp Val Arg Gln Ala Pro Gly Gln Gly Leu Glu Trp Ile
        35              40              45

Gly Val Ile Tyr Pro Gly Ser Gly Gly Thr Asn Tyr Asn Glu Lys Phe
    50              55              60

Lys Gly Arg Val Thr Leu Thr Val Asp Glu Ser Thr Asn Thr Ala Tyr
65              70              75              80

Met Glu Leu Ser Ser Leu Arg Ser Glu Asp Thr Ala Val Tyr Phe Cys
            85              90              95

Ala Arg Arg Asp Gly Asn Tyr Gly Trp Phe Ala Tyr Trp Gly Gln Gly
            100             105             110

Thr Leu Val Thr Val Ser Ser
            115
```

( 2 ) INFORMATION FOR SEQ ID NO:11:

( i ) SEQUENCE CHARACTERISTICS:
      ( A ) LENGTH: 119 amino acids
      ( B ) TYPE: amino acid
      ( D ) TOPOLOGY: linear ( i i ) MOLECULE TYPE: protein ( v ) FRAGMENT TYPE: N-terminal fragment ( x i ) SEQUENCE DESCRIPTION: SEQ ID NO:11:

```
Gln Val Gln Leu Gln Gln Ser Gly Ala Glu Leu Val Gly Pro Gly Thr
 1               5              10              15

Ser Val Arg Val Ser Cys Lys Ala Ser Gly Tyr Ala Phe Thr Asn Tyr
            20              25              30

Leu Ile Glu Trp Val Lys Gln Arg Pro Gly Gln Gly Leu Glu Trp Ile
        35              40              45

Gly Val Ile Tyr Pro Gly Ser Gly Gly Thr Asn Tyr Asn Glu Lys Phe
```

|  | 50 |  |  |  | 55 |  |  |  |  | 60 |  |  |  |  |
|---|---|---|---|---|---|---|---|---|---|---|---|---|---|---|
| Lys 65 | Gly | Lys | Ala | Thr 70 | Leu | Thr | Val | Asp | Lys 75 | Ser | Ser | Thr | Thr | Ala | Tyr 80 |
| Met | Gln | Leu | Ser | Ser 85 | Leu | Thr | Ser | Asp | Ser 90 | Ala | Val | Tyr | Phe 95 | Cys |
| Ala | Arg | Arg | Asp 100 | Gly | Asn | Tyr | Gly | Trp 105 | Phe | Ala | Tyr | Trp | Gly 110 | Arg | Gly |
| Thr | Leu | Val 115 | Thr | Val | Ser | Ala |

( 2 ) INFORMATION FOR SEQ ID NO:12:

( i ) SEQUENCE CHARACTERISTICS:
        ( A ) LENGTH: 214 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:12:

| Asp 1 | Ile | Gln | Met | Thr 5 | Gln | Thr | Pro | Ser | Thr 10 | Leu | Ser | Ala | Ser | Val 15 | Gly |
|---|---|---|---|---|---|---|---|---|---|---|---|---|---|---|---|
| Asp | Arg | Val | Thr 20 | Ile | Ser | Cys | Arg | Ala 25 | Ser | Gln | Asp | Ile | Asn 30 | Asn | Tyr |
| Leu | Asn | Trp 35 | Tyr | Gln | Gln | Lys | Pro 40 | Gly | Lys | Ala | Pro | Lys 45 | Leu | Leu | Ile |
| Tyr | Tyr 50 | Thr | Ser | Thr | Leu | His 55 | Ser | Gly | Val | Pro | Ser 60 | Arg | Phe | Ser | Gly |
| Ser 65 | Gly | Ser | Gly | Thr | Asp 70 | Tyr | Thr | Leu | Thr | Ile 75 | Ser | Ser | Leu | Gln | Pro 80 |
| Asp | Asp | Phe | Ala | Thr 85 | Tyr | Phe | Cys | Gln | Gln 90 | Gly | Asn | Thr | Leu | Pro 95 | Trp |
| Thr | Phe | Gly | Gln 100 | Gly | Thr | Lys | Val | Glu 105 | Val | Lys | Arg | Thr | Val 110 | Ala | Ala |
| Pro | Ser | Val 115 | Phe | Ile | Phe | Pro | Pro 120 | Ser | Asp | Glu | Gln | Leu 125 | Lys | Ser | Gly |
| Thr | Ala 130 | Ser | Val | Val | Cys | Leu 135 | Leu | Asn | Asn | Phe | Tyr 140 | Pro | Arg | Glu | Ala |
| Lys 145 | Val | Gln | Trp | Lys | Val 150 | Asp | Asn | Ala | Leu | Gln 155 | Ser | Gly | Asn | Ser | Gln 160 |
| Glu | Ser | Val | Thr | Glu 165 | Gln | Asp | Ser | Lys | Asp 170 | Ser | Thr | Tyr | Ser | Leu 175 | Ser |
| Ser | Thr | Leu | Thr 180 | Leu | Ser | Lys | Ala | Asp 185 | Tyr | Glu | Lys | His | Lys 190 | Val | Tyr |
| Ala | Cys | Glu 195 | Val | Thr | His | Gln | Gly 200 | Leu | Ser | Ser | Pro | Val 205 | Thr | Lys | Ser |
| Phe | Asn 210 | Arg | Gly | Glu | Cys |

( 2 ) INFORMATION FOR SEQ ID NO:13:

( i ) SEQUENCE CHARACTERISTICS:
        ( A ) LENGTH: 449 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 | |
| Ser | Val | Lys | Val | Ser | Cys | Lys | Ala | Ser | Gly | Tyr | Ala | Phe | Thr | Asn | Tyr |
| | | | 20 | | | | | 25 | | | | | 30 | | |
| Leu | Ile | Glu | Trp | Val | Arg | Gln | Ala | Pro | Gly | Gln | Gly | Leu | Glu | Trp | Ile |
| | | | 35 | | | | | 40 | | | | | 45 | | |
| Gly | Val | Ile | Tyr | Pro | Gly | Ser | Gly | Gly | Thr | Asn | Tyr | Asn | Glu | Lys | Phe |
| | | | 50 | | | | | 55 | | | | | 60 | | |
| Lys | Gly | Arg | Val | Thr | Leu | Thr | Val | Asp | Glu | Ser | Thr | Asn | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Phe | Cys |
| | | | | 85 | | | | | 90 | | | | | 95 | |
| Ala | Arg | Arg | Asp | Gly | Asn | Tyr | Gly | Trp | Phe | Ala | Tyr | Trp | Gly | Gln | Gly |
| | | | | 100 | | | | | 105 | | | | | 110 | |
| Thr | Leu | Val | Thr | Val | Ser | Ser | Ala | Ser | Thr | Lys | Gly | Pro | Ser | Val | Phe |
| | | | 115 | | | | | 120 | | | | | 125 | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | | 195 | | | | | 200 | | | | | 205 | | |
| Ser | Asn | Thr | Lys | Val | Asp | Lys | Lys | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | | 275 | | | | | 280 | | | | | 285 | | |
| Ala | Lys | Thr | Lys | Pro | Arg | Glu | Glu | Gln | Tyr | Asn | Ser | Thr | Tyr | Arg | Val |
| | 290 | | | | | 295 | | | | | 300 | | | | |
| Val | Ser | Val | Leu | Thr | Val | Leu | His | Gln | Asp | Trp | Leu | Asn | Gly | Lys | Glu |
| 305 | | | | | 310 | | | | | 315 | | | | | 320 |
| Tyr | Lys | Cys | Lys | Val | Ser | Asn | Lys | Ala | Leu | Pro | Ala | Pro | Ile | Glu | Lys |
| | | | | 325 | | | | | 330 | | | | | 335 | |
| Thr | Ile | Ser | Lys | Ala | Lys | Gly | Gln | Pro | Arg | Glu | Pro | Gln | Val | Tyr | Thr |
| | | | 340 | | | | | 345 | | | | | 350 | | |
| Leu | Pro | Pro | Ser | Arg | Asp | Glu | Leu | Thr | Lys | Asn | Gln | Val | Ser | Leu | Thr |
| | | | 355 | | | | | 360 | | | | | 365 | | |
| Cys | Leu | Val | Lys | Gly | Phe | Tyr | Pro | Ser | Asp | Ile | Ala | Val | Glu | Trp | Glu |
| | 370 | | | | | 375 | | | | | 380 | | | | |
| Ser | Asn | Gly | Gln | Pro | Glu | Asn | Asn | Tyr | Lys | Thr | Thr | Pro | Pro | Val | Leu |
| 385 | | | | | 390 | | | | | 395 | | | | | 400 |
| Asp | Ser | Asp | Gly | Ser | Phe | Phe | Leu | Tyr | Ser | Lys | Leu | Thr | Val | Asp | Lys |
| | | | | 405 | | | | | 410 | | | | | 415 | |

| Ser | Arg | Trp | Gln | Gln | Gly | Asn | Val | Phe | Ser | Cys | Ser | Val | Met | His | Glu |
|-----|-----|-----|-----|-----|-----|-----|-----|-----|-----|-----|-----|-----|-----|-----|-----|
|     |     |     | 420 |     |     |     |     | 425 |     |     |     |     | 430 |     |     |

| Ala | Leu | His | Asn | His | Tyr | Thr | Gln | Lys | Ser | Leu | Ser | Leu | Ser | Pro | Gly |
|-----|-----|-----|-----|-----|-----|-----|-----|-----|-----|-----|-----|-----|-----|-----|-----|
|     |     | 435 |     |     |     |     | 440 |     |     |     |     | 445 |     |     |     |

Lys ( 2 ) INFORMATION FOR SEQ ID NO:14:

( i ) SEQUENCE CHARACTERISTICS:
        ( A ) LENGTH: 113 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: synthetic DNA ( x i ) SEQUENCE DESCRIPTION: SEQ ID NO:14:

```
TATATCTAGA CCACCATGGG ATGGAGCTGG ATCTTTCTCT TCCTCCTGTC AGGTACCGCG     60
GGCGTGCACT CTCAGGTCCA GCTTGTCCAG TCTGGCGCTG AAGTCAAGAA ACC           113
```

( 2 ) INFORMATION FOR SEQ ID NO:15:

( i ) SEQUENCE CHARACTERISTICS:
        ( A ) LENGTH: 123 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: synthetic DNA ( x i ) SEQUENCE DESCRIPTION: SEQ ID NO:15:

```
TATAGAATTC TCGAGACCCT GTCCAGGGGC CTGCCTTACC CACTCTATCA AGTAATTAGT     60
AAAGGCGTAG CCAGAAGCTT TGCAGGAGAC CTTCACGGAG CTCCCAGGTT TCTTGACTTC    120
AGC                                                                  123
```

( 2 ) INFORMATION FOR SEQ ID NO:16:

( i ) SEQUENCE CHARACTERISTICS:
        ( A ) LENGTH: 141 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: synthetic DNA ( x i ) SEQUENCE DESCRIPTION: SEQ ID NO:16:

```
TATAGAATTC TCGAGTGGAT TGGAGTGATT TATCCTGGAA GTGGTGGTAC TAACTACAAT     60
GAGAAGTTCA AGGGCCGTGT TACACTGACA GTAGACGAAT CCACCAATAC AGCCTACATG    120
GAACTGAGCA GCCTGAGATC A                                              141
```

( 2 ) INFORMATION FOR SEQ ID NO:17:

( i ) SEQUENCE CHARACTERISTICS:
        ( A ) LENGTH: 137 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: synthetic DNA ( x i ) SEQUENCE DESCRIPTION: SEQ ID NO:17:

| TATATCTAGA | GGTTTTAAGG | ACTCACCTGA | GGAGACTGTG | ACCAGGGTTC | CTTGGCCCCA | 60 |
| GTAGGCAAAC | CATCCGTAGT | TACCATCTCG | TCTTGCACAG | AAATAGACTG | CAGTGTCCTC | 120 |
| TGATCTCAGG | CTGCTCA | | | | | 137 |

( 2 ) INFORMATION FOR SEQ ID NO:18:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: synthetic DNA ( x i ) SEQUENCE DESCRIPTION: SEQ ID NO:18:

| TATATCTAGA | CCACCATGGA | GACCGATACC | CTCCTGCTAT | GGGTCCTCCT | GCTATGGGTC | 60 |
| CCAGGATCAA | CCGGAGATAT | TCAGATGACC | CAGACTCCGT | CGACCCTCTC | TGCTAGC | 117 |

( 2 ) INFORMATION FOR SEQ ID NO:19:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: synthetic DNA ( x i ) SEQUENCE DESCRIPTION: SEQ ID NO:19:

| TATAAAGCTT | GGGAGCTTTG | CCTGGCTTCT | GCTGATACCA | GTTTAAATAA | TTGTTAATGT | 60 |
| CCTGACTTGC | CCTGCAACTT | ATGGTGACCC | TATCCCCGAC | GCTAGCAGAG | AGGGTCG | 117 |

( 2 ) INFORMATION FOR SEQ ID NO:20:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: synthetic DNA ( x i ) SEQUENCE DESCRIPTION: SEQ ID NO:20:

| TATAAAGCTT | CTAATTTATT | ACACATCAAC | ATTACACTCA | GGGGTACCTT | CACGCTTCAG | 60 |
| TGGCAGTGGA | TCTGGGACCG | ATTATACCCT | CACAATCTCG | AGTCTGCAGC | CAGATGA | 117 |

( 2 ) INFORMATION FOR SEQ ID NO:21:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: Other nucleic acid
        ( A ) DESCRIPTION: synthetic DNA ( x i ) SEQUENCE DESCRIPTION: SEQ ID NO:21:

| TATATCTAGA | GCAAAAGTCT | ACTTACGTTT | GACCTCCACC | TTGGTCCCCT | GACCGAACGT | 60 |
| CCACGGAAGC | GTATTACCCT | GTTGGCAAAA | ATAAGTGGCG | AAATCATCTG | GCTGCAGACT | 120 |

( 2 ) INFORMATION FOR SEQ ID NO:22:

( i ) SEQUENCE CHARACTERISTICS:
- ( A ) LENGTH: 222 amino acids
- ( B ) TYPE: amino acid
- ( C ) STRANDEDNESS: single
- ( D ) TOPOLOGY: linear ( i i ) MOLECULE TYPE: protein ( x i ) SEQUENCE DESCRIPTION: SEQ ID NO:22:

```
Gln Val Gln Leu Val Gln Ser Gly Ala Glu Val Lys Lys Pro Gly Ser
  1               5                  10                  15
Ser Val Lys Val Ser Cys Lys Ala Ser Gly Tyr Ala Phe Thr Asn Tyr
             20                  25                  30
Leu Ile Glu Trp Val Arg Gln Ala Pro Gly Gln Gly Leu Glu Trp Ile
         35                  40                  45
Gly Val Ile Tyr Pro Gly Ser Gly Gly Thr Asn Tyr Asn Glu Lys Phe
     50                  55                  60
Lys Gly Arg Val Thr Leu Thr Val Asp Glu Ser Thr Asn Thr Ala Tyr
 65                  70                  75                  80
Met Glu Leu Ser Ser Leu Arg Ser Glu Asp Thr Ala Val Tyr Phe Cys
                 85                  90                  95
Ala Arg Arg Asp Gly Asn Tyr Gly Trp Phe Ala Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys
        210                 215                 220
```

( 2 ) INFORMATION FOR SEQ ID NO:23:

( i ) SEQUENCE CHARACTERISTICS:
- ( A ) LENGTH: 235 amino acids
- ( B ) TYPE: amino acid
- ( C ) STRANDEDNESS: single
- ( D ) TOPOLOGY: linear ( i i ) MOLECULE TYPE: protein ( x i ) SEQUENCE DESCRIPTION: SEQ ID NO:23:

```
Gln Val Gln Leu Val Gln Ser Gly Ala Glu Val Lys Lys Pro Gly Ser
  1               5                  10                  15
Ser Val Lys Val Ser Cys Lys Ala Ser Gly Tyr Ala Phe Thr Asn Tyr
             20                  25                  30
Leu Ile Glu Trp Val Arg Gln Ala Pro Gly Gln Gly Leu Glu Trp Ile
         35                  40                  45
Gly Val Ile Tyr Pro Gly Ser Gly Gly Thr Asn Tyr Asn Glu Lys Phe
     50                  55                  60
Lys Gly Arg Val Thr Leu Thr Val Asp Glu Ser Thr Asn Thr Ala Tyr
 65                  70                  75                  80
```

```
Met  Glu  Leu  Ser  Ser  Leu  Arg  Ser  Glu  Asp  Thr  Ala  Val  Tyr  Phe  Cys
                    85                       90                      95

Ala  Arg  Arg  Asp  Gly  Asn  Tyr  Gly  Trp  Phe  Ala  Tyr  Trp  Gly  Gln  Gly
               100                      105                     110

Thr  Leu  Val  Thr  Val  Ser  Ser  Ala  Ser  Thr  Lys  Gly  Pro  Ser  Val  Phe
          115                     120                    125

Pro  Leu  Ala  Pro  Ser  Ser  Lys  Ser  Thr  Ser  Gly  Gly  Thr  Ala  Ala  Leu
     130                     135                    140

Gly  Cys  Leu  Val  Lys  Asp  Tyr  Phe  Pro  Glu  Pro  Val  Thr  Val  Ser  Trp
145                 150                      155                          160

Asn  Ser  Gly  Ala  Leu  Thr  Ser  Gly  Val  His  Thr  Phe  Pro  Ala  Val  Leu
                    165                      170                     175

Gln  Ser  Ser  Gly  Leu  Tyr  Ser  Leu  Ser  Ser  Val  Val  Thr  Val  Pro  Ser
               180                      185                     190

Ser  Ser  Leu  Gly  Thr  Gln  Thr  Tyr  Ile  Cys  Asn  Val  Asn  His  Lys  Pro
          195                      200                     205

Ser  Asn  Thr  Lys  Val  Asp  Lys  Lys  Val  Glu  Pro  Lys  Ser  Cys  Asp  Lys
     210                     215                     220

Thr  His  Thr  Cys  Pro  Pro  Cys  Pro  Ala  Pro  Glu
225                      230                     235
```